US012774346B2

(12) United States Patent
Mo et al.

(10) Patent No.: US 12,774,346 B2
(45) Date of Patent: Oct. 27, 2026

(54) ANTI-CEACAM5 MONOCLONAL ANTIBODY AND PREPARATION METHOD THEREOF AND USE THEREOF

(71) Applicant: BIOTHEUS INC., Zhuhai (CN)

(72) Inventors: Shifu Mo, Shanghai (CN); Wei Xu, Shanghai (CN); Yi Luo, Zhuhai (CN); Liandi Chen, Zhuhai (CN)

(73) Assignee: BIOTHEUS INC., Zhuhai (CN)

( * ) Notice: Subject to any disclaimer, the term of this patent is extended or adjusted under 35 U.S.C. 154(b) by 1086 days.

(21) Appl. No.: 17/596,183

(22) PCT Filed: Jun. 3, 2020

(86) PCT No.: PCT/CN2020/094045
§ 371 (c)(1),
(2) Date: Dec. 3, 2021

(87) PCT Pub. No.: WO2020/244526
PCT Pub. Date: Dec. 10, 2020

(65) Prior Publication Data
US 2022/0242968 A1 Aug. 4, 2022

(30) Foreign Application Priority Data
Jun. 4, 2019 (CN) ......................... 201910481112.6

(51) Int. Cl.
*C07K 16/30* (2006.01)
*A61K 39/00* (2006.01)
(Continued)

(52) U.S. Cl.
CPC .......... *C07K 16/3007* (2013.01); *A61K 40/11* (2025.01); *A61K 40/31* (2025.01);
(Continued)

(58) Field of Classification Search
CPC ............ C07K 16/3007; C07K 2317/10; C07K 2317/24; C07K 2317/56; C07K 2317/565;
(Continued)

(56) References Cited

U.S. PATENT DOCUMENTS

2015/0125386 A1 5/2015 Hansen et al.
2016/0108131 A1 4/2016 Berne et al.
(Continued)

FOREIGN PATENT DOCUMENTS

CN 102482701 A 5/2012
CN 103987729 A 8/2014
(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995) (Year: 1995).*
(Continued)

*Primary Examiner* — Aurora M Fontainhas
*Assistant Examiner* — Selam Berhane
(74) *Attorney, Agent, or Firm* — Michele V. Frank; Keith G. Haddaway; Venable LLP

(57) ABSTRACT

Disclosed are a monoclonal antibody and antigen-binding fragment thereof which can specifically bind to human carcinoembryonic antigen-related cell adhesion molecule 5 (CEACAM5); also disclosed is a chimeric antigen receptor based on said antibody, and a method for preparing said antibody and antigen-binding fragment and use thereof for treating CEACAM5-related tumors.

33 Claims, 8 Drawing Sheets

Specification includes a Sequence Listing.

(51) Int. Cl.

| | |
|---|---|
| ***A61K 40/11*** | (2025.01) |
| ***A61K 40/31*** | (2025.01) |
| ***A61K 40/42*** | (2025.01) |
| ***A61K 47/68*** | (2017.01) |
| ***A61P 35/00*** | (2006.01) |
| ***C12N 15/85*** | (2006.01) |
| ***G01N 33/575*** | (2026.01) |

(52) U.S. Cl.

CPC ...... *A61K 40/4266* (2025.01); *A61K 47/6849* (2017.08); *A61P 35/00* (2018.01); *C12N 15/85* (2013.01); *G01N 33/57565* (2026.01); *A61K 2039/505* (2013.01); *A61K 2239/31* (2023.05); *A61K 2239/38* (2023.05); *A61K 2239/50* (2023.05); *C07K 2317/10* (2013.01); *C07K 2317/24* (2013.01); *C07K 2317/56* (2013.01); *C07K 2317/565* (2013.01); *C07K 2317/732* (2013.01); *C07K 2317/92* (2013.01)

(58) Field of Classification Search

CPC .......... C07K 2317/732; C07K 2317/92; A61K 47/6849; A61K 40/4266; A61K 40/31; A61K 40/11; A61K 2239/50; A61K 2239/31; A61K 2239/38; A61K 2039/505; A61P 35/00; C12N 15/85; G01N 33/57473

See application file for complete search history.

(56) References Cited

U.S. PATENT DOCUMENTS

| | | | | |
|---|---|---|---|---|
| 2017/0355756 | A1* | 12/2017 | Julien | C07K 16/18 |
| 2018/0162940 | A1 | 6/2018 | Willuda et al. | |
| 2020/0123270 | A1 | 4/2020 | Doihra et al. | |

FOREIGN PATENT DOCUMENTS

| | | | | | |
|---|---|---|---|---|---|
| CN | 102482701 | B * | 5/2015 | A61K 39/39558 |
| CN | 104918958 | A | 9/2015 | |
| CN | 107106683 | A | 8/2017 | |
| CN | 107743495 | A | 2/2018 | |
| CN | 108341876 | A | 7/2018 | |
| CN | 109180815 | A | 1/2019 | |
| EP | 3009455 | A1 | 4/2016 | |
| EP | 3199552 | A1 | 8/2017 | |
| JP | 2018-522833 | A | 8/2018 | |
| WO | 03/080672 | A1 | 10/2003 | |
| WO | WO-2008068048 | A2 * | 6/2008 | A61P 31/10 |
| WO | 2011034660 | A1 | 3/2011 | |
| WO | 2013/054320 | A1 | 4/2013 | |
| WO | 2013054320 | A | 4/2013 | |
| WO | 2015/069430 | A2 | 5/2015 | |
| WO | 2016/150899 | A2 | 9/2016 | |
| WO | 2019/009388 | A1 | 10/2019 | |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003) (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017) (Year: 2017).*

Kussie, Paul H., "A Single Engineered Amino Acid Substitution Changes Antibody Fine Specificity", 1994, Journal of Immunology 152(1): pp. 146-152. (Year: 1994) (Year: 1994).*

International Search Report and Written Opinion from PCT/CN2020/094049 mailed Sep. 4, 2020.

Extended European Search Report dated May 8, 2023, directed to EP Patent Application No. 20818729.4; 10 pages.

Search Report in First Office Action dated Jun. 1, 2023, directed to CN Patent Application No. 202080040435.2; (pp. 6-7 of 8 pages).

Furukawa A. et al., (Jan. 2004), GenBank: BAE71460.1: "Immunoglobulin H-chain V-region, partial [Mus musculus]," National Library of Medicine; 1 page.

June, C.H. et al., (Mar. 2018), "CAR T cell immunotherapy for human cancer," Science, vol. 359, No. 6382, pp. 1361-1365.

Madhusoodanan, J. (Feb. 2018), "With New CAR T Approach, City of Hope CEACAM Comes Full Circle," retrieved on Aug. 29, 2019, located at <https://www.cityofhope.org/breakthroughs/ceacam-research-comes-full-circule-thanks-to-new-car-t-approach>; 3 pages.

First Office Action dated Sep. 15, 2023, directed to TW Patent Application No. 109118629; 4 pages.

Notification to Grant Patent Right for Invention dated Dec. 29, 2023, directed to CN Patent Application No. 202080040435.2; 6 pages.

Liu, Yinjie et al., (Apr. 30, 2007). "Preparation and Biological Activity Analysis of Monoclonal Antibodies Against Human DR5,"; pp. 355-356.

Office Action dated Feb. 8, 2024, directed to Canadian Patent Application No. 3142635; 7 pages.

Notice of Grounds of Rejection mailed Mar. 5, 2024, directed to Japanese Patent Application No. 2021-572365; 22 pages.

Rudikoff, S. et al., (Mar. 1982). "Single amino acid substitution altering antigen-binding specificity," Proceedings of the National Academy of Sciences, vol. 79, pp. 1979-1983.

Tamura, M. et al., (Feb. 2000). "Structural Correlates of an Anticarcinoma Antibody: Identification of Specificity-Determining Residues (SDRs) and Development of a Minimally Immunogenic Antibody Variant by Retention of SDRs Only," The Journal of Immunology, vol. 164, p. 1432-41.

Search Report and Opinion mailed Jun. 30, 2026, directed to BR Patent Application No. 112021024544-8; 5 pages.

* cited by examiner

| | UM05-5L |
|---|---|
| EC50 | 105.3 |

ANTI-CEACAM5 MONOCLONAL ANTIBODY AND PREPARATION METHOD THEREOF AND USE THEREOF

This application is a National Stage Application under 35 U.S.C. § 371 PCT/CN2020/094045, filed Jun. 3, 2020, which claims priority benefit from Chinese Patent Application No. 201910481112.6, filed on Jun. 4, 2019, the entire content of which is incorporated herein by reference. All references cited anywhere in this specification, including the Background and Detailed Description sections, are incorporated by reference as if each had been individually incorporated.

SEQUENCE LISTING

The instant application contains a Sequence Listing which has been filed electronically in ASCII format and is hereby incorporated by reference in its entirety. Said ASCII copy, created on Dec. 29, 2021, is named 141279_555265_SL.txt and is 17,814 bytes in size.

TECHNICAL FIELD

The present application belongs to the field of immunity, and specifically relates to a monoclonal antibody and antigen-binding fragment thereof that can specifically bind to human carcinoembryonic antigen cell adhesion molecule 5 (CEACAM5). The present application also relates to a preparation method and use of the antibody and antigen-binding fragment thereof.

BACKGROUND

The human carcinoembryonic antigen cell adhesion molecule (CEACAM) family was discovered as early as the 1960s, including 35 genes/pseudogenes located on chromosome 19 (between q13.1 and 13.3), among which there are 21 that encode proteins. CEACAM belongs to the immunoglobulin superfamily of adhesion molecules, its domains are highly glycosylated and usually comprises 1 to 2 immunoglobulin variable region-like domains (N domains) and 0 to 6 immunoglobulin constant region-like domains. CEACAM proteins locate on the cell membrane, in which CEACAM1, CEACAM3 and CEACAM4 are anchored on the cell membrane through a hydrophobic transmembrane domain; while CEACAM5-8 are anchored on the cell membrane through glycosyl-phosphatidyl-inositol. These extracellular domains usually act as adhesion molecules between cells (for example, epithelium, endothelium, dendrites, and leukocytes).

CEACAM involves a variety of cell functions, regulates cell growth and differentiation through signal transduction based on the adhesion function between cells, and plays an important role in insulin homeostasis, angiogenesis and immune regulation. Members of the CEACAM family are involved in a variety of pathophysiological roles, including as receptors for microbial pathogens. They play an important role in carcinogenesis, especially in cancer detection, progression and metastasis. CEACAM5 (referred to as CEA, also known as CD66e) is a glycoprotein with a molecular weight of about 180 kDa. CEACAM5 containing 7 domains anchors on the cell membrane via glycosyl-phosphatidyl-inositol (GPI). The 7 domains include a single N-terminal Ig variable domain and 6 domains (A1-B1-A2-B2-A3-B3) homologous to the Ig constant domain. CEACAM5 was originally thought to be a protein expressed in fetal tissues, and has now been identified in several normal adult tissues. Overexpression of CEACAM5 has been observed in many types of cancer. For example, CEACAM5 can be detected in the blood of patients with colon cancer. Moreover, further studies have determined that its overexpression is associated with many malignant tumors, and often correlates with poor prognosis. In prostate cancer and colorectal cancer, the overexpression of CEACAM5 is also found and could be used as a tumor biomarker.

In addition, CEACAM5/CEACAM6 have also been found to be overexpressed in a variety of malignant tumors, such as breast, pancreas, ovarian, colon, lung and gastric gland tumors, and are related to tumor invasion and metastasis. During the initiation of liver metastasis, CEACAM5 binds to its receptor CEAr, and their interaction leads to the activation and production of pro-inflammatory cytokines, mainly IL-1, IL-6, IL-10 and TNF-α. In short, these cytokines change the microenvironment of hepatocytes and Kupffer cells, as well as their interaction with hepatic sinusoidal cells. These interactions not only affect tumor cells or other liver cells, but also seem to promote the vitality of CSC and other circulating tumor cells in the cerebrospinal fluid.

Based on this, in addition to the current application of using CEACAM5 as a tumor marker in an immunological assay that measures elevated CEACAM5 level in the blood of cancer patients for clinically determining prognosis of cancers and monitoring progress of cancers, it becomes more important that CEACAM5 is a potentially useful tumor-associated antigen for targeted therapy. There are two major applications that have been reported to use CEACAM5 for targeted immunotherapy in cancer. One application uses an anti-CEACAM5 antibody to trigger the lytic activity of immune cells, especially through antibody-dependent cytotoxicity (ADCC) or complement-dependent cytotoxicity (CDC), so as to eliminate tumor cells expressing CEACAM5; the other application comprises conjugating an anti-CEACAM5 antibody or antibody fragment thereof with an effector molecule such as drug, toxin, radioactive nucleotide, immunomodulator or cytokine to specifically target a tumor cell expressing CEACAM5, thereby exerting the therapeutic effect of the effector molecule. Based on the fact that CEACAM5 is preferentially overexpressed in some solid tumors such as colorectal cancer, pancreatic cancer, lung cancer, gastric cancer, hepatocellular tumor, breast cancer and thyroid cancer, current research focuses on the antigen recognition ability of anti-CEACAM5 antibodies.

In conclusion, the current research shows that immunotherapy targeting CEACAM5 will help to inhibit tumor metastasis. In particular, antibodies with strong specificity to CEACAM5 can better avoid the side effects caused by the off-target of the antibodies. For example, CEACAM1 and CEACAM3, CEACAM8 are widely distributed in the human immune system and bone marrow, such as neutrophils, etc., and a specific CEACAM5 and/or CEACAM6 antibody can reduce the possible side effects of drugs and increase the treatment window.

Based on this, there is a demand for anti-CEACAM antibodies with higher affinity and better specificity.

Contents of the Invention

In the present application, unless otherwise specified, the scientific and technical terms used herein have the meanings commonly understood by those skilled in the art. In addition, the laboratory procedures of cell culture, molecular genetics, nucleic acid chemistry, and immunology used herein are all routine procedures widely used in the corresponding fields. At the same time, in order to better understand the present application, definitions and explanations of related terms are provided below.

Definition of Terms

The term "antibody" in the present application includes any immunoglobulin, monoclonal antibody, polyclonal antibody, multispecific antibody or bispecific (bivalent) antibody that can bind to a specific antigen. A natural intact antibody contains two heavy chains and two light chains. Each heavy chain is composed of one variable region and first, second and third constant regions; each light chain is composed of one variable region and one constant region. The mammalian heavy chains can be divided into α, δ, ε, γ and μ, and the mammalian light chains can be divided into λ or κ. The antibody is presented in "Y" type, and the neck of the Y-type structure is composed of the second and third constant regions of the two heavy chains, which are linked by disulfide bonds. Each arm of the "Y" type structure contains the variable region and the first constant region of one of the heavy chains, which are linked with the variable region and constant region of one light chain. The variable regions of the light and heavy chains determine antigen-binding. The variable region of each chain contains three hypervariable regions, called complementarity determining regions (CDRs). The CDRs of the light chain (L) include VLCDR1, VLCDR2, and VLCDR3, and the CDRs of the heavy chain (H) include VHCDR1, VHCDR2, and VHCDR3. The CDR boundaries of the antibody and antigen-binding fragment thereof disclosed in the present application can be named or identified by Kabat, Chothia or Al-Lazikani numbering system. (Al-Lazikani, B., Chothia, C., Lesk, A M, J. Mol. Biol., 273(4): 927 (1997); Chothia, C., etc., J. Mol. Biol., 186(3): 651-63 (1985); Chothia, C. and Lesk, A M, J. Mol. Biol., 196: 901 (1987); Chothia, C. et al., Nature, 342(6252): 877-83 (1989); Kabat, E A, etc., National Institutes of Health, Bethesda, Md. (1991)). Wherein, the three CDRs are separated by a continuous side part called framework region (FR). The framework region is more highly conserved than the CDRs and forms a scaffold to support the hypervariable loop. The constant regions of heavy and light chains are not related to the antigen-binding, but have multiple effector functions. Antibodies can be divided into several categories based on the amino acid sequence of the constant region of the heavy chain. According to whether they contain α, δ, ε, γ and μ heavy chains, antibodies can be divided into five main categories or isomers: IgA, IgD, IgE, IgG, and IgM. Several major antibody categories can further be divided into subclasses, such as IgG1 (γ1 heavy chain), IgG2 (γ2 heavy chain), IgG3 (γ3 heavy chain), IgG4 (γ4 heavy chain), IgA1 (α1 heavy chain) or IgA2 (α2 heavy chain) and so on.

The term "antigen-binding fragment" in the present application refers to an antibody fragment formed by an antibody portion containing one or more CDRs or any other antibody fragment that binds to an antigen but does not have a complete antibody structure. Examples of antigen-binding fragment include, but are not limited to, such as diabody, Fab, Fab', $F(ab')_2$, Fv fragment, disulfide bond-stabilized Fv fragment (dsFv), $(dsFv)_2$, dual-specific dsFv (dsFv-dsFv'), disulfide bond-stabilized difunctional antibody (ds diabody), single-chain antibody molecule (scFv), scFv dimer (bivalent bifunctional antibody), bivalent single-chain antibody (BsFv), multispecific antibody, camelized single domain antibody, nanobody, domain antibody and bivalent domain antibody. The antigen-binding fragment can bind to the same antigen as the parent antibody. In some embodiments, the antigen-binding fragment may contain one or more CDRs from a specific human antibody, which are grafted into a framework region derived from one or more different human antibodies.

The "Fab" fragment of an antibody refers to a part of the antibody molecule, which is composed of a light chain (including the variable and constant regions), and a variable region and part of a constant region of a heavy chain that are ligated via disulfide bonds.

The "Fab'" fragment refers to a Fab fragment that contains a part of the hinge region.

"$F(ab')_2$" refers to a dimer of Fab.

The Fc segment of an antibody is responsible for a variety of different effector functions such as ADCC and CDC, but does not participate in antigen-binding.

The "Fv" segment of an antibody refers to the smallest antibody fragment that contains a complete antigen-binding site. The Fv fragment is composed of a variable region of a light chain and a variable region of a heavy chain.

The "single-chain Fv antibody" or "scFv" refers to an engineered antibody in which a variable region of a light chain and a variable region of a heavy chain are directly ligated or ligated through a peptide chain (Huston J S et al., Proc Natl Acad Sci USA, 85: 5879 (1988)).

The "single-chain antibody Fv-Fc" or "scFv-Fc" refers to an engineered antibody composed of scFv that is ligated to a Fc segment of a certain antibody.

The "camelized single domain antibody", "heavy-chain antibody" or "HCAb (heavy-chain-only antibodies, HCAb)" all refer to antibodies containing two VH domains without light chain (Riechmann L. and Muyldermans S., J Immunol Methods. 231(1-2): 25-38 (1999); Muyldermans S., J Biotechnol. 74(4): 277-302 (2001); W094/04678; W094/25591; U.S. Pat. No. 6,005,079). The heavy chain antibodies were originally derived from camelids (camels, dromedaries, and llamas). Although their light chains are missing, camelized antibodies have confirmed antigen-binding functions (Hamers Casterman C. et al., Nature 363 (6428): 446-8 (1993); Nguyen V K. et al., "Heavy-chain antibodies in Camelidae: a case of evolutionary innovation, Immunogenetics. 54 (1): 39-47 (2002); Nguyen V K. et al., Immunology. 109 (1): 93-101 (2003)). The variable region of heavy chain antibody (VH domain) is the smallest known antigen-binding unit produced by acquired immunity (Koch-Nolte F. et al., FASEB J. 21 (13): 3490-8. Epub (2007)).

The "nanobody" refers to an antibody fragment, which is composed of a VH domain derived from a heavy chain antibody and two constant regions CH2 and CH3.

The "diabody" contains a small antibody fragment with two antigen-binding sites, in which the fragment contains a VH domain and a VL domain ligated to the same polypeptide chain (see, Holliger P. et al., Proc Natl. Acad Sci US A. 90(14): 6444-8 (1993); EP404097; W093/11161). The linker between the two domains is so short that the two domains on the same chain cannot be paired with each other, which forces the two domains to pair with the complementary domains of the other chain to form two antibody binding sites. These two antibody binding sites can target the same or different antigens (or epitopes).

The "domain antibody" refers to an antibody fragment containing only one heavy chain variable region or one light chain variable region. In some cases, two or more VH domains are covalently linked by a polypeptide linker to form a bivalent domain antibody. The two VH domains of a bivalent domain antibody can target the same or different antigens.

In some embodiments, "$(dsFv)_2$" contains three peptide chains: two VH genes are linked by a polypeptide linker, and they are ligated to two VL groups by disulfide bonds.

In some embodiments, the "bispecific ds bifunctional antibody" contains VL1-VH2 (linked by a polypeptide linker) and VH1-VL2 (also linked by a polypeptide linker), and the two are linked between VH1 and VL1 via disulfide bonds.

The "dual-specific dsFv" or "dsFv-dsFv" contains three polypeptide chains: VH1-VH2 group, in which the heavy chains of the two are linked by a polypeptide linker (for example, a long elastic linker), and they are respectively ligated to VL1 and VL2 groups via disulfide bonds, and each pair of heavy and light chains paired with disulfide bonds has a different antigen specificity.

In certain embodiments, the "scFv dimer" is a bivalent difunctional antibody or bivalent single-chain antibody (BsFv), containing two dimerized VH-VL (linked by a polypeptide linker) groups, wherein the VH of one group and the VL of the other group cooperate to form two binding sites, and the two binding sites can target to the same antigen (or epitope) or different antigens (or epitopes). In other embodiments, the "scFv dimer" is a dual-specific difunctional antibody that contains VL1-VH2 (linked by a polypeptide linker) and VH1-VL2 (linked by a polypeptide linker), wherein VH1 and VL1 cooperate, VH2 and VL2 cooperate, and each cooperated pair has a different antigen specificity.

For the term "fully human" used in the present application, when it is applied to an antibody or antigen-binding fragment, it refers to that the antibody or antigen-binding fragment has a certain amino acid sequence or consists of the amino acid sequence, in which the amino acid sequence corresponds to an amino acid sequences of an antibody that is produced by a human or a human immune cell, or derived from a non-human source such as a transgenic non-human animal using a human antibody library, or other sequence encoding a human antibody. In some embodiments, the fully human antibody does not contain amino acid residues (especially antigen-binding residues) derived from a non-human antibody.

For the term "humanized" used in the present application, when it is applied to an antibody or antigen-binding fragment, it refers to that an antibody or antigen-binding fragment that contains a CDR derived from a non-human animal, a FR region derived from human, and a constant region derived from human (when applicable). Since a humanized antibody or antigen-binding fragment has a reduced immunogenicity, it can be used as a human therapeutic in certain embodiments. In some embodiments, the non-human animal is a mammal such as a mouse, rat, rabbit, goat, sheep, guinea pig, or hamster. In some embodiments, the humanized antibody or antigen-binding fragment consists essentially of human sequences, except that the CDR sequence is non-human. In some embodiments, the FR region derived from human may contain the same amino acid sequence as the human antibody from which it is derived, or it may contain some amino acid changes, for example, no more than 10, 9, 8, 7, 6, 5, 4, 3, 2 or 1 amino acid change. In some embodiments, the amino acid change may be present only in the FR region of the heavy chain, only in the FR region of the light chain, or in both chains. In some preferred embodiments, the humanized antibody comprises human FR1-3 and human JH and JK.

The term "chimeric" as used in the present application refers to an antibody or antigen-binding fragment in which a part of a heavy chain and/or light chain is derived from one species, and the remaining part of the heavy chain and/or light chain is derived from a different species. In an illustrative example, a chimeric antibody may contain a constant region derived from a human and a variable region derived from a non-human animal such as a mouse.

The term "carcinoembryonic antigen cell adhesion molecule 5" (CEACAM5, abbreviated as CEA, also known as CD66e; see, for example, AAA51967.1/GI: 180223, 702 amino acids) refers to a glycoprotein with a molecular weight of about 180 kDa. CEACAM5 contains 7 Ig-like domains, these 7 domains comprise a single N-terminal Ig variable domain and 6 domains (A1-B1-A2-B2-A3-B3) that are homologous to Ig constant domain. CEACAM is anchored on the cell membrane via the carboxy-terminal glycosyl-phosphatidyl-inositol (GPI).

The "specifically bind" or "specific binding" in the present application refers to a non-random binding reaction between two molecules, such as a reaction between an antibody and an antigen. In some embodiments, the antibody or antigen-binding fragment thereof of the present application specifically binds to a human and/or monkey carcinoembryonic antigen cell adhesion molecule 5, and its binding affinity (KD) is $\leq 10^{-6}$M. KD. In the present application, KD refers to a ratio of dissociation rate to binding rate (koff/kon), which can be measured by surface plasmon resonance, for example, using an instrument such as Biacore.

The "selective binding" in the present application refers to that the antibody or antigen-binding fragment thereof of the present application specifically binds to a CEACAM5 protein, but does not substantially bind or binds at a significantly lower level to another CEACAM protein, such as CEACAM1 protein, CEACAM3 Protein, CEACAM7 protein.

In some embodiments, the heavy chain constant region of the antibody described in the present application is of human IgG1 type. In some embodiments, the light chain constant region of the antibody described in the present application is a κ chain. In some embodiments, the heavy chain and light chain constant regions of the antibody described in the present application are human IgG1 and κ chain, respectively.

In the present application, when "conservative substitution" is applied to an amino acid sequence, it refers to that one amino acid residue is replaced with another amino acid residue, in which they have a side chain with similar physical and chemical properties. For example, a conservation substitution may be performed between amino acid residues with hydrophobic side chain (for example, Met, Ala, Val, Leu and Ile), between residues with neutral hydrophilic side chain (for example, Cys, Ser, Thr, Asn and Gln), between residues with acidic side chain (for example, Asp, Glu), between amino acids with basic side chain (for example, His, Lys, and Arg), or between residues with aromatic side chain (for example, Trp, Tyr, and Phe). It is known in the art that a conservative substitution usually does not cause significant changes in the conformational structure of the protein, and therefore the biological activity of the protein can be retained.

When "percent sequence identity" is applied to an amino acid sequence (or nucleic acid sequence), it refers to that after sequence alignment is performed, and intervals are introduced when necessary to maximize the number of identical amino acids (or nucleic acids), the percentage of the amino acid (or nucleic acid) residues of a candidate sequence that are identical to the amino acid (or nucleic acid) residues of a reference sequence. The amino acid residues of conservative substitution may or may not be considered as the identical residues. The sequence alignment can be performed by tools disclosed in the art to determine the percent sequence identity of amino acid (or nucleic acid) sequences. Those skilled in the art can use the default parameters of the tools or adjust the parameters appropriately according to the needs of the alignment, for example, by selecting a suitable algorithm.

The "T cell" used in the present application includes $CD4^+$ T cell, $CD8^+$ T cell, T helper type 1 T cell, T helper type 2 T cell, T helper type 17 T cell, and suppressor T cell.

The "effector function" as used in the present application refers to the biological activity of the Fc region of an antibody binding to its effector such as C1 complex and Fc receptor. Exemplary effector function includes complement-dependent cytotoxicity (CDC) induced by the interaction of the antibody with C1q on the C1 complex, antibody-dependent cell-mediated cytotoxicity (ADCC) induced by the binding of the Fc region of the antibody to the Fc receptor on the effector cell, and phagocytosis.

The "cancer" or "cancerous symptom" in the present application refers to any medical condition that is mediated by tumor or malignant cell growth, proliferation or metastasis, and causes a solid tumor and non-solid tumor such as leukemia. The "tumor" in the present application refers to a solid substance of tumor and/or malignant cell.

The "treatment" or "therapy" of a certain condition comprises preventing or alleviating a certain condition, reducing the rise or development rate of a certain condition, reducing the risk of developing a certain condition, and preventing or delaying the development of a symptom associated with a certain condition, reducing or terminating a symptom associated with a certain condition, producing a complete or partial reversal of a certain condition, curing a certain condition, or any combination thereof. For a cancer, the "treatment" or "therapy" can refer to inhibiting or slowing the growth, reproduction or metastasis of tumor or malignant cells, or any combination of some of the above. For a tumor, the "treatment" or "therapy" comprises removing all or part of the tumor, inhibiting or slowing the growth and metastasis of the tumor, preventing or delaying the development of the tumor, or combination of some of the above.

The "isolated" material refers to that it has been artificially changed from its natural state. If a certain "isolated" substance or component appears in nature, it has been changed or deviated from its original state, or both. For example, polynucleotides or polypeptides naturally occurring in a living animal has not been isolated, but if these polynucleotides or polypeptides are sufficiently separated from the coexisting substances in their natural state and exist in a sufficiently pure state, they can be considered as being "isolated". In some embodiments, the purity of antibody and antigen-binding fragment thereof is at least 90%, 93%, 95%, 96%, 97%, 98%, 99%, which can be determined by electrophoresis methods (for example, SDS-PAGE, isoelectric focusing, capillary electrophoresis), or chromatography (for example, ion exchange chromatography or reverse phase HPLC).

The "vector" in the present application refers to a vehicle into which a polynucleotide encoding a certain protein can be operatively inserted to allow the protein be expressed. The vector can be used to transform, transduce or transfect a host cell so that a genetic material element it carries can be expressed in the host cell. For example, the vector includes: plasmid, phagemid, cosmid, artificial chromosome such as yeast artificial chromosome (YAC), bacterial artificial chromosome (BAC) or P1-derived artificial chromosome (PAC), bacteriophage such as λ phage or M13 bacteriophage, and animal virus, etc. The types of animal virus used as vector include retrovirus (including lentivirus, adenovirus, adeno-associated virus, herpes virus (for example, herpes simplex virus), poxvirus, baculovirus, papilloma virus, papilloma vacuole virus (for example, SV40). The vector may contain a variety of elements that control expression, including promoter sequence, transcription initiation sequence, enhancer sequence, selection element and reporter gene. In addition, the vector may also contain a replication origin. The vector may also contain a component that assists it to enter the cell, including but not limited to, viral particle, liposome, or protein shell.

In the present application, "a host cell" refers to a cell into which an exogenous polynucleotide and/or vector is introduced. The host cell described in the present application includes, but is not limited to, prokaryotic cell such as *E. coli* or *Bacillus subtilis*, fungal cell such as yeast cell or *Aspergillus*, insect cell such as S2 *Drosophila* cell or Sf9, or animal cell such as fibroblast, CHO cell, COS cell, NSO cell, HeLa cell, BHK cell, HEK 293 cell or human cell.

In the present application, "chimeric antigen receptor" is referred to as CAR, which refers to a cell surface receptor that can recognize a specific antigen (for example, a tumor antigen), which comprises an extracellular domain for recognizing the specific antigen (for example, an antigen-binding fragment that can recognize and bind to the specific antigen) and an intracellular domain for transmit an extracellular signal to inside of the cell (also referred to as intracellular signal transduction region, for example, the δ chain of CD3 or the intracellular part of FcεRIγ). The T cell that carries and expresses such chimeric antigen receptor is called CAR-T cell, which can recognize and bind to the specific antigen and a cell (for example, tumor cell) expressing the specific antigen through the extracellular domain, and by the intracellular signal transduction function, it can activate immune response, release a large number of various effectors, and efficiently kills a cell expressing the specific antigen (for example, tumor cell), thereby exerting a therapeutic effect (for example, treatment of tumor).

Based on the shortcomings of the prior art, one of the main objects of the present application is to provide an anti-CEACAM5 antibody with stronger specificity and better selectivity. The present application also provides a preparation method and use of the antibody, and the anti-CEACAM5 antibody of the present application can be used for detection and/or treatment of a tumor.

Antibody of the Present Application

In one aspect, the present application provides an antibody or antigen-binding fragment thereof that specifically binds to CEACAM5 protein, wherein the antibody or antigen-binding fragment thereof comprises:

(a) a heavy chain variable region (VH) comprising the following 3 complementarity determining regions (CDRs):

(i) VH CDR1, which consists of the following sequence: SEQ ID NO: 1, or a sequence having a substitution, deletion or addition of one or several amino acids (for example, a substitution, deletion or addition of 1, 2 or 3 amino acids) as compared therewith, (ii) VH CDR2, which consists of the following sequence: SEQ ID NO: 2, or a sequence having a substitution, deletion or addition of one or several amino acids (for example, a substitution, deletion or addition of 1, 2 or 3 amino acids) as compared therewith, and (iii) VH CDR3, which consists of the following sequence: SEQ ID NO: 3, or a sequence having a substitution, deletion or addition of one or several amino acids (for example, a substitution, deletion or addition of 1, 2 or 3 amino acids) as compared therewith;

and/or, (b) a light chain variable region (VL) comprising the following 3 complementarity determining regions (CDRs):

(iv) VL CDR1, which consists of the following sequence: SEQ ID NO: 4, or a sequence having a substitution, deletion or addition of one or several amino acids (for example, a substitution, deletion or addition of 1, 2 or 3 amino acids) as compared therewith, (v) VL CDR2, which consists of the following sequence: SEQ ID NO: 5, or a sequence having a substitution, deletion or addition of one or several amino acids (for example, a substitution, deletion or addition of 1, 2 or 3 amino acids) as compared therewith, and (vi) VL CDR3, which consists of the following sequence: SEQ ID NO: 6, or a sequence having a substitution, deletion or addition of one or several amino acids (for example, a substitution, deletion or addition of 1, 2 or 3 amino acids) as compared therewith.

In certain embodiments, the substitution described in any one of (i) to (vi) is a conservative substitution.

In certain embodiments, the CDRs described in any one of (i) to (vi) are defined according to the Kabat numbering system.

In certain embodiments, the antibody or antigen-binding fragment thereof comprises the following three heavy chain CDRs: VH CDR1 having a sequence as shown in SEQ ID NO: 1 or SEQ ID NO: 20, VH CDR2 having a sequence as shown in SEQ ID NO: 2 or SEQ ID NO: 21, and VH CDR3 having a sequence as shown in SEQ ID NO: 3; and/or, the following three light chain CDRs: VL CDR1 having a sequence as shown in SEQ ID NO: 4, VL CDR2 having a sequence as shown in SEQ ID NO: 5 or SEQ ID NO: 22, and VL CDR3 having a sequence as shown in SEQ ID NO: 6.

In certain embodiments, the antibody or antigen-binding fragment thereof comprises the following three heavy chain CDRs: VH CDR1 having a sequence as shown in SEQ ID NO: 1, VH CDR2 having a sequence as shown in SEQ ID NO: 2, and VH CDR3 having a sequence as shown in SEQ ID NO: 3; and/or, the following three light chain CDRs: VL CDR1 having a sequence as shown in SEQ ID NO: 4, VL CDR2 having a sequence as shown in SEQ ID NO: 5, and VL CDR3 having a sequence as shown in SEQ ID NO: 6.

In certain embodiments, the antibody or antigen-binding fragment thereof comprises the following three heavy chain CDRs: VH CDR1 having a sequence as shown in SEQ ID NO: 20, VH CDR2 having a sequence as shown in SEQ ID NO: 21, and VH CDR3 having a sequence as shown in SEQ ID NO: 3; and/or, the following three light chain CDRs: VL CDR1 having a sequence as shown in SEQ ID NO: 4, VL CDR2 having a sequence as shown in SEQ ID NO: 22, and VL CDR3 having a sequence as shown in SEQ ID NO: 6.

In certain embodiments, the heavy chain CDRs and light chain CDRs are defined according to the Kabat numbering system.

In one aspect, the present application provides an antibody or antigen-binding fragment thereof that specifically binds to CEACAM5 protein, wherein the antibody or antigen-binding fragment thereof comprises:

(i) VH CDR1 as contained in a heavy chain variable region (VH) as shown in SEQ ID NO: 7, or a sequence having a substitution, deletion or addition of one or several amino acids (for example, a substitution, deletion or addition of 1, 2 or 3 amino acids) as compared therewith;

(ii) VH CDR2 as contained in a heavy chain variable region (VH) as shown in SEQ ID NO: 7, or a sequence having a substitution, deletion or addition of one or several amino acids (for example, a substitution, deletion or addition of 1, 2 or 3 amino acids) as compared therewith; and, (iii) VH CDR3 as contained in a heavy chain variable region (VH) as shown in SEQ ID NO: 7, or a sequence having a substitution, deletion or addition of one or several amino acids (for example, a substitution, deletion or addition of 1, 2 or 3 amino acids) as compared therewith; and/or, (iv) VL CDR1 as contained in a light chain variable region (VL) as shown in SEQ ID NO: 8, or a sequence having a substitution, deletion or addition of one or several amino acids (for example, a substitution, deletion or addition of 1, 2 or 3 amino acids) as compared therewith;

(v) VL CDR2 as contained in a light chain variable region (VL) as shown in SEQ ID NO: 8, or a sequence having a substitution, deletion or addition of one or several amino acids (for example, a substitution, deletion or addition of 1, 2 or 3 amino acids) as compared therewith; and, (vi) VL CDR3 as contained in a light chain variable region (VL) as shown in SEQ ID NO: 8, or a sequence having a substitution, deletion or addition of one or several amino acids (for example, a substitution, deletion or addition of 1, 2 or 3 amino acids) as compared therewith; and/or.

In certain embodiments, the 3 CDRs contained in the VH and/or the 3 CDRs contained in the VL are defined by the Kabat, IMGT or Chothia numbering system. In certain embodiments, the 3 CDRs contained in the VH and/or the 3 CDRs contained in the VL are defined by the Kabat numbering system.

In certain embodiments, the antibody or antigen-binding fragment thereof comprises:

(a) a heavy chain variable region (VH), which comprises an amino acid sequence selected from the following:

(i) the sequence shown in SEQ ID NO: 7;

(ii) a sequence having a substitution, deletion or addition of one or several amino acids (for example, a substitution, deletion or addition of 1, 2, 3, 4 or 5 amino acids) as compared with the sequence shown in SEQ ID NO: 7; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence shown in SEQ ID NO: 7;

and/or (b) a light chain variable region (VL), which comprises an amino acid sequence selected from the following:

(iv) the sequence shown in SEQ ID NO: 8;

(v) a sequence having a substitution, deletion or addition of one or several amino acids (for example, a substitution, deletion or addition of 1, 2, 3, 4 or 5 amino acids) as compared with the sequence shown in SEQ ID NO: 8; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence shown in SEQ ID NO: 8.

In certain embodiments, the substitution described in (ii) or (v) is a conservative substitution.

In certain embodiments, the antibody or antigen-binding fragment thereof comprises a heavy chain framework region sequence and/or a light chain framework region sequence derived from a human immunoglobulin.

In certain embodiments, the antibody or antigen-binding fragment thereof comprises: a heavy chain framework region sequence encoded by a human heavy chain germline gene, and/or a light chain framework region sequence encoded by a human light chain germline gene.

In certain exemplary embodiments, the antibody or antigen-binding fragment thereof comprises: VH comprising the sequence shown in SEQ ID NO: 7, SEQ ID NO: 16, SEQ ID NO: 18 or SEQ ID NO: 19 and VL comprising the sequence shown in SEQ ID NO: 8 or SEQ ID NO: 17.

In certain exemplary embodiments, the antibody or antigen-binding fragment thereof comprises: VH having the sequence shown in SEQ ID NO: 7 and VL having the sequence shown in SEQ ID NO: 8. In certain exemplary embodiments, the antibody or antigen-binding fragment thereof comprises: VH having the sequence shown in SEQ ID NO: 18 and VL having the sequence shown in SEQ ID NO: 8. In certain exemplary embodiments, the antibody or antigen-binding fragment thereof comprises: VH having the sequence shown in SEQ ID NO: 16 and VL having the sequence shown in SEQ ID NO: 17. In certain exemplary embodiments, the antibody or antigen-binding fragment thereof comprises: VH having the sequence shown in SEQ ID NO: 19 and VL having the sequence shown in SEQ ID NO: 17.

The antibody or antigen-binding fragment thereof of the present application may comprise a constant region sequence derived from a mammalian (for example, murine or human) immunoglobulin or a variant thereof, in which the variant has a substitution, deletion or addition of one or several amino acids or any combination thereof (for example, a substitution, deletion or addition of at most 20, at most 15, at most 10, or at most 5 amino acids, or any combination thereof; for example, a substitution, deletion or addition of 1, 2, 3, 4 or 5 amino acids, or any combination thereof) as compared with the sequence from which it is derived.

In certain embodiments, the antibody or antigen-binding fragment thereof of the present application has a heavy chain comprising a heavy chain constant region (CH) of a human immunoglobulin or a variant thereof, wherein the variant has a substitution, deletion or addition of one or several amino acids or any combination thereof (for example, a substitution, deletion or addition of at most 20, at most 15, at most 10, or at most 5 amino acids, or any combination thereof; for example, a substitution, deletion or addition of 1, 2, 3, 4 or 5 amino acids, or any combination thereof) as compared with the sequence from which it is derived; and/or, in certain embodiments, the antibody or antigen-binding fragment thereof of the present application has a light chain comprising a light chain constant region (CL) of a human immunoglobulin or a variant thereof, wherein the variant has a substitution, deletion or addition of one or several amino acids or any combination thereof (for example, a substitution, deletion or addition of at most 20, at most 15, at most 10, or at most 5 amino acids, or any combination thereof; for example, a substitution, deletion or addition of 1, 2, 3, 4 or 5 amino acids, or any combination thereof) as compared with the sequence from which it is derived.

In some embodiments, the variant of the heavy chain constant region (CH) may have conservative substitution of one or several amino acids (for example, conservative substitution of 1, 2, 3, 4 or 5 amino acids) as compared with the sequence from which it is derived.

In some embodiments, the variant of the light chain constant region (CL) may have conservative substitution of one or several amino acids (for example, conservative substitution of 1, 2, 3, 4 or 5 amino acids) as compared with the sequence from which it is derived.

In certain embodiments, the heavy chain constant region is an IgG heavy chain constant region, such as IgG1, IgG2, IgG3, or IgG4 heavy chain constant region. In certain embodiments, the heavy chain constant region is a human IgG1, IgG2, IgG3, or IgG4 heavy chain constant region.

In certain embodiments, the light chain constant region is a κ light chain constant region. In certain embodiments, the light chain constant region is a human κ light chain constant region.

In certain exemplary embodiments, the antibody or antigen-binding fragment thereof of the present application comprises a heavy chain constant region (CH) shown in SEQ ID NO: 9; and/or, a light chain constant region (CL) shown in SEQ ID NO: 11.

In certain embodiments, the antigen-binding fragment is selected from the group consisting of Fab, Fab', $(Fab')_2$, Fv, disulfide-linked Fv, scFv, diabody, and single domain antibody (sdAb).

In certain embodiments, the antibody is a murine antibody, chimeric antibody, humanized antibody, bispecific antibody, or multispecific antibody.

The antibody or antigen-binding fragment thereof of the present application has one or more activities selected from the following:

(1) specifically binding to CEACAM5 protein or a cell expressing CEACAM5 protein;

(2) basically not binding to CEACAM1, CEACAM3, CEACAM7, CEACAM8 proteins or a cell expressing CEACAM1, CEACAM3, CEACAM7, CEACAM8 proteins;

(3) only weakly binding to CEACAM6 protein or a cell expressing CEACAM6 protein, in which the binding affinity is significantly lower than the binding affinity to CEACAM5 protein or a cell expressing CEACAM5 protein;

(4) having ADCC activity;

(5) capable of inhibiting or killing a tumor cell expressing CEACAM5 protein (for example, colon cancer cell, gastric cancer cell), thereby having tumor treatment activity.

In certain embodiments, the antibody or antigen-binding fragment thereof of the present application comprises a label. In some embodiments, the antibody or antigen-binding fragment thereof comprises a detectable label, such as enzyme (for example, horseradish peroxidase), radionuclide, fluorescent dye, luminescent substance (for example, chemiluminescent substance) or biotin.

In certain embodiments, the present application provides an exemplary anti-CEACAM5 antibody UM05-5L and hUM05-3.

Those skilled in the art should understand that the aforementioned CDR sequences can be modified to include substitution of one or more amino acids, thereby obtaining improved biological activity such as improved binding affinity to human carcinoembryonic antigen cell adhesion molecule 5. For example, the phage display technology can be used to produce and express an antibody variant library (for example, Fab or FcFv variants), and then screen for an antibody that has affinity with CEACAM5. In another example, computer software can be used to simulate the binding of the antibody to CEACAM5 and identify the amino acid residues on the antibody that form the binding interface. The substitution of these residues may be avoided to prevent a decrease in binding affinity, or these residues can be targeted for substitution to form stronger binding. In certain embodiments, at least one (or all) substitutions in the CDR sequences is conservative substitution.

In certain embodiments, the antibody or antigen-binding fragment comprises one or several CDR sequences, and these CDR sequences have a sequence identity of at least 80% (for example, at least 85%, 88%, 90%, 91%, 92%, 93%, 94%, 95%, 96%, 97%, 98%, 99%) as compared with SED ID NO: 1-6, and at the same time retain similar or even higher binding affinity to CEACAM5 as compared with their parent antibody. The parent antibody has substantially the same sequences, but its corresponding CDR sequences have a sequence identity of 100% compared with the sequences listed in SEQ ID NO: 1-6.

In some embodiments, the antibody or antigen-binding fragment described in the present application can specifically bind to CEACAM5 with a binding affinity (KD) of $\leq 10^{-7}$M, which can be measured by surface plasmon resonance. The binding affinity value can be expressed by a KD value, which is obtained by the calculation of a ratio of dissociation rate to binding rate (koff/kon) when the binding of the antigen to the antigen-binding molecule reaches equilibrium. The antigen-binding affinity (for example, KD) can be appropriately determined by a suitable method known in the art, for example, a plasmon resonance binding method comprising the use of an instrument such as Biacore.

In some embodiments, the antibody or antigen-binding fragment described in the present application binds to CEACAM5 at an EC50 (i.e., half-binding concentration) of 1 ng/mL to 10 μg/mL. The binding of the antibody or antigen-binding fragment to CEACAM5 can be determined by a method known in the art, such as a sandwich method such as ELISA, Western blot, FACS or other binding assays. In an exemplary example, the antibody to be tested (i.e., primary antibody) is bound to immobilized CEACAM5 or cells expressing CEACAM5, then the unbound antibody is washed away, and a labeled secondary antibody is introduced, which can bind to the primary antibody, and therefore the bound secondary antibody is detected. When immobilized carcinoembryonic antigen cell adhesion molecule 5 is used, the detection can be performed on a microplate reader, or when cells expressing CEACAM5 are used, FACS analysis can be used for the detection.

In some embodiments, the antibody or antigen-binding fragment described in the present application binds to CEACAM5 at an EC50 (i.e., effective concentration of 50%) of 10 ng/mL to 10 μg/mL (determined by FACS analysis).

The antibody is specific for CEACAM5. In certain embodiments, the antibody optionally does not bind to CEACAM1, CEACAM3, CEACAM7, CEACAM8 and binds to CEACAM6 with a binding affinity that is significantly lower than that of CEACAM5.

In some embodiments, the antibody described in the present application can be used in combination with an immunogenic substance, such as tumor cell, purified tumor antigen, cells transfected with encoding immunostimulatory factor, and tumor vaccine. In addition, the anti-CEACAM5 antibody and antigen-binding fragment thereof can be comprised in a combination therapy, including standard chemotherapy and radiation therapy, target-based small molecule therapy, and other emerging immune checkpoint modulator therapy. In some embodiments, the antibody and antigen-binding fragment thereof can be used as a basic molecule of antibody-drug conjugate, bispecific or multivalent antibody.

In some embodiments, the antibody and antigen-binding fragment thereof described in the present application is camelized single chain domain antibody, diabody, scFv, scFv dimer, BsFv, dsFv, $(dsFv)_2$, dsFv-dsFv', Fv fragment, Fab, Fab', $F(ab')_2$, ds diabody, nanobody, domain antibody or bivalent domain antibody.

In some embodiments, the antibody described in the present application comprises an immunoglobulin constant region. In some embodiments, the immunoglobulin constant region comprises a heavy chain and/or light chain constant region. The heavy chain constant region comprises CH1, CH1-CH2 or CH1-CH3 regions. In some embodiments, the immunoglobulin constant region may further comprise one or more modifications to obtain a desired property. For example, the constant region can be modified to reduce or eliminate one or several effector functions, enhance FcRn receptor binding, or introduce one or several cysteine residues.

In some embodiments, the antibody and antigen-binding fragment thereof further comprises a conjugate. It is conceivable that the antibody or antigen-binding fragment thereof of the present application can be linked to a variety of conjugates (see, for example, "Conjugate Vaccines", Contributions to Microbiology and Immunology, J M Cruse and R E Lewis, Jr. (eds.), Carger Press, New York (1989)). These conjugates can be linked to the antibody or antigen-binding fragment by other means such as covalent binding, affinity binding, embedding, coordinate binding, complexation, binding, mixing or addition. In some embodiments, the antibody and antigen-binding fragment disclosed in the present application can be engineered to contain specific sites other than the epitope binding portion, and these sites can be used to bind one or several conjugates. For example, such a site may comprise one or several reactive amino acid residues, such as cysteine residues and histidine residues, to facilitate covalent attachment to the conjugate. In certain embodiments, the antibody may be attached to the conjugate indirectly, or be attached to the conjugate through another conjugate. For example, the antibody or antigen-binding fragment thereof can bind to biotin and then indirectly bind to a second conjugate, which is linked to avidin. The conjugate may be a detectable label, pharmacokinetic modification part, purification part or cytotoxic part. Examples of detectable label may include fluorescent label (for example, fluorescein, rhodamine, dansyl, phycoerythrin or Texas red), enzyme substrate label (for example, horseradish peroxidase, alkaline phosphatase), luciferase, glucoamylase, lysozyme, glucose oxidase or β-D galactosidase), stable isotope or radioisotope, chromophore moiety, digoxin, biotin/avidin, DNA molecule or gold for testing. In certain embodiments, the conjugate may be a pharmacokinetic modification part such as PEG, which helps extend the half-life of the antibody. Other suitable polymers include, for example, carboxymethyl cellulose, dextran, polyvinyl alcohol, polyvinylpyrrolidone, ethylene glycol/propylene glycol copolymer, and the like. In some embodiments, the conjugate may be a purified part such as magnetic beads. The "cytotoxic part" can be any agent that is harmful to a cell or may damage or kill a cell. Examples of the cytotoxic part include, but are not limited to, paclitaxel, cytochalasin B, gramicidin D, ethidium bromide, emetine, mitomycin, etoposide, teniposide, vincristine, vinblastine, colchicine, doxorubicin, daunorubicin, dihydroxy-anthracin-dione, mitoxantrone, mithramycin, actinomycin D, 1-dehydrotestosterone, glucocorticoid, procaine, tetracaine, lidocaine, propranolol, puromycin and analogue thereof, antimetabolite (for example, methotrexate, 6-mercaptopurine, 6-mercaptoguanine, cytarabine, 5-fluorouracil, dacarbazine), alkylating agent (for example, chlormethine, thiotepa chlorambucil, melphalan, carmustine (BSNU) and lomustine (CCNU), cyclophosphamide, Busulfan, dibromomannitol, streptozotocin, mitomycin C, and cis-dichlorodiamine platinum (DDP) cisplatin), anthracycline antibiotic (for example, daunorubicin (formerly known as daunomycin) and adriamycin), antibiotic (for example, dactinomycin (formerly known as actinomycin), bleomycin, mithramycin, and ampicillin (AMC)), and antimitotic agent (for example, vincristine and vinblastine).

Nucleic Acid Molecule and Recombination Method

The antibody of the present application can be prepared by various methods known in the art, for example, obtained by genetic engineering recombination technology. For example, a DNA molecule encoding the antibody or antigen-binding fragment thereof of the present application can be obtained by chemical synthesis or PCR amplification. The resulting DNA molecule is inserted into an expression vector and then transfected into a host cell. Then, the transfected host cell is cultured under a specific condition, and the antibody or antigen-binding fragment thereof of the present application is expressed.

The antigen-binding fragment of the present application can be obtained by hydrolyzing an intact antibody molecule (see Morimoto et al., J. Biochem. Biophys. Methods 24:107-117 (1992); and Brennan et al., Science 229:81 (1985)). In addition, these antigen-binding fragments can also be directly produced by recombinant host cells (reviewed in Hudson, Curr. Opin. Immunol. 11: 548-557 (1999); Little et al., Immunol. Today, 21: 364-370 (2000))). For example, Fab' fragments can be obtained directly from the host cells; Fab' fragments can be chemically coupled to form $F(ab')_2$ fragments (Carter et al., Bio/Technology, 10: 163-167 (1992)). In addition, Fv, Fab or $F(ab')_2$ fragments can also be directly isolated from the recombinant host cell culture medium. Those of ordinary skill in the art are fully aware of other techniques for preparing these antigen-binding fragments.

In some specific embodiments, the preparation method of the anti-CEACAM5 antibody or antigen-binding fragment thereof provided in the present application comprises the following steps:

1) using a Balb/c mouse immunized with a CHO cell line overexpressing carcinoembryonic antigen cell adhesion molecule 5 as a material, extracting and fusing a spleen cell with a mouse myeloma cell line SP2/0-AG14 to obtain a hybridoma cell line capable of expressing anti-CEACAM5 antibody or antigen-binding fragment thereof;
2) cloning and expressing a gene of anti-CEACAM5 antibody or antigen-binding fragment thereof in the hybridoma cell line obtained in step 1);
3) providing an expression vector, the expression vector comprising the gene cloned in step 2) and an expression control sequence operatively ligated to the gene;
4) transforming a host cell with the expression vector described in step 3);
5) culturing the host cell obtained in step 4);
6) separating and purifying to obtain a monoclonal antibody.

In another aspect, the present application provides a hybridoma cell line used in the above preparation method.

In the present application, a human-mouse hybridoma that secretes a specific anti-CEACAM5 antibody is prepared, the heavy chain and light chain sequences (100% human genes) of the antibody are cloned by using molecular biology techniques, and an anti-human carcinoembryonic antigen cell adhesion molecule 5 human monoclonal antibody is constructed, that the antibody is expressed and produced by CHO cells. Compared with existing antibodies, these antibodies as drugs have stronger binding capacity and specificity.

In another aspect, the present application provides an isolated nucleic acid molecule, which comprises a nucleotide sequence encoding the antibody or antigen-binding fragment thereof of the present application, or the heavy chain variable region of and/or light chain variable region thereof. In certain embodiments, the nucleic acid molecule comprises a nucleotide coding sequence as shown in SEQ ID NO: 14 and/or SEQ ID NO: 15.

In another aspect, the present application provides a vector (for example, cloning vector or expression vector), which comprises the isolated nucleic acid molecule as described above. In certain embodiments, the vector of the present application is a plasmid, cosmid, bacteriophage, or the like.

In certain embodiments, the vector comprises a first nucleotide sequence encoding a heavy chain variable region of the antibody or antigen-binding fragment thereof of the present application, and/or a second nucleotide sequence encoding a light chain variable region of the antibody or antigen-binding fragment thereof of the present application. In some embodiments, the first nucleotide sequence and the second nucleotide sequence are provided on the same or different vectors.

In another aspect, the present application provides a host cell, which comprises the isolated nucleic acid molecule or vector as described above. In certain embodiments, the host cell is a mammalian cell. In certain embodiments, the host cell is a human, murine, sheep, horse, dog, or cat cell. In certain embodiments, the host cell is a Chinese hamster ovary cell.

In another aspect, a method for preparing the antibody or antigen-binding fragment thereof of the present application is provided, which comprises culturing the host cell as described above under a condition that allows expression of the antibody or antigen-binding fragment thereof, and recovering the antibody or antigen-binding fragment thereof from a culture of the host cell.

In another aspect, the present application also provides a bispecific or multispecific molecule, which comprises the antibody or antigen-binding fragment thereof. In certain embodiments, the bispecific or multispecific molecule specifically binds to CEACAM5, and additionally specifically binds to one or several other targets. In certain embodiments, the bispecific or multispecific molecule further comprises at least one molecule (for example, a second antibody) with a second binding specificity for a second target.

In another aspect, the present application also provides an immunoconjugate, which comprises the antibody or antigen-binding fragment thereof and a therapeutic agent conjugated to the antibody or antigen-binding fragment thereof. In certain embodiments, the therapeutic agent is selected from cytotoxic agents. In certain embodiments, the therapeutic agent is selected from the group consisting of alkylating agent, mitotic inhibitor, anti-tumor antibiotic, antimetabolite, topoisomerase inhibitor, tyrosine-kinase inhibitor, radionuclide agent, and any combination thereof. In certain embodiments, the immunoconjugate is an antibody-drug conjugate (ADC).

Using genetic engineering techniques well-known in the art, an amino acid sequence of the antibody and antigen-binding fragment thereof described in the present application can be converted into a corresponding DNA coding sequence. Due to the degeneracy of the genetic code, the DNA sequence obtained by the conversion may not be completely consistent, while the encoded protein sequence remains unchanged.

Using recombinant techniques well-known in the art, a vector comprising a polynucleotide encoding the antibody and antigen-binding fragment thereof can be introduced into a host cell for cloning (amplification of DNA) or gene expression. In another embodiment, the antibody and antigen-binding fragment thereof can be prepared by homologous recombination methods known in the art. A variety of vectors are available. Vector components usually include, but are not limited to, two or more of the following: signal sequence, replication origin, one or several marker genes, enhancer sequence, promoters (for example: SV40, CMV, EF-1a) and transcription termination sequence.

In some embodiments, the vector system includes mammalian, bacterial, yeast system, etc., and will comprise vectors such as plasmids, including but not limited to pALTER, pBAD, pcDNA, pCal, pL, pELpGEMEX, pGEX, pCLpCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2 and other vectors that can be obtained from laboratories or are commercially available. Suitable vector may include plasmid or viral vector (for example, replication-defective retrovirus, adenovirus, and adeno-associated virus).

The vector comprising a polynucleotide encoding the antibody and antigen-binding fragment thereof can be introduced into a host cell for cloning or gene expression. The host cell suitable for cloning or expressing the DNA in the vector in the present application is a prokaryotic cell, yeast or the above-mentioned higher eukaryotic cell. Prokaryotic cell suitable for use in the present application includes eubacteria, such as Gram-negative bacteria or Gram-positive bacteria, such as Enterobacteriaceae (for example, *Escherichia coli*), *Enterobacter* spp., *Erwinia* spp., *Klebsiella* spp., *Proteus* spp., *Salmonella* spp. such as *Salmonella typhimurium, Serratia* spp. such as *Serratia marcescens*, and *Shigella* spp., and *Bacillus* spp. such as *Bacillus subtilis* and *Bacillus licheniformis, Pseudomonas* spp. such as *Pseudomonas aeruginosa* and *Streptomyces.*

In addition to prokaryotic cells, eukaryotic microorganisms such as filamentous fungi or yeast can also be used as host cells for cloning or expressing the vector encoding the antibody. *Saccharomyces cerevisiae*, or bread yeast, is the most commonly used lower eukaryotic host microorganism. However, many other genera, species and strains are more commonly used and applicable in the present application, such as *Schizosaccharomyces pombe; Kluyveromyces* hosts such as *Kluyveromyces lactis, Kluyveromyces fragilis* (ATCC12424), *Kluyveromyces bulgaricus* (ATCC16045), *Kluyveromyces weichii* (ATCC24178), *Kluyveromyces* (ATCC56500), *Kluyveromyces drosophila* (ATCC36906), *Kluyveromyces thermotolerans* and *Kluyveromyces marxianus: Yarrowia lipolytica* (EP402226); *Pichia pastoris* (EP183070); *Candida: Trichoderma reesei* (EP244234); *Neurospora*; Schwann yeast, such as: *Schwanniomyces occidentalis*; and filamentous fungi, such as *Neurospora, Penicillium, Curvularia*, and *Aspergillus*, such as *Aspergillus nidulans* and *Aspergillus niger.*

The host cell suitable for expressing glycosylated antibody or antigen-binding fragment thereof provided in the present application is derived from a multicellular organism. Examples of invertebrate cells include plant and insect cells. A variety of baculoviral strains and their variants, as well as the corresponding permissive insect host cells, have been discovered, from hosts such as the following: *Spodoptera frugiperda* (caterpillar), *Aedes aegypti* (mosquito), *Aedes albopictus* (mosquito), *Drosophila melanogaster* (drosophila) and *Bombyx mori* (silkworm). A variety of virus strains used for transfection are publicly available, such as *Autographa californica* nuclear polyhedrosis virus and Bm-5 variant of *Bombyx mori* nuclear polyhedrosis virus. These viruses can be used in the present application, especially used to transfect *Spodoptera frugiperda* cells. Plant cell cultures of cotton, corn, potato, soybean, petunia, tomato and tobacco can also be used as hosts.

However, the most interesting is spinal cells, and the cultivation of spinal cells (tissue culture) has become a routine operation. Examples of available mammalian host cells include SV40-transformed monkey kidney cell line CV1 (COS-7, ATCC CRL 1651); human embryonic kidney cell line (293 or suspension cultured 293 cell subclone, Graham et al., J. Gen Virol. 36:59 (1977)); young hamster kidney cell (B blood, ATCC CCL 10); Chinese hamster ovary cell/-DHFR (CHO, Urlaub et al., Proc. Natl. Acad. Sci. USA 77: 4216 (1980)); mouse sertoli cell (TM4, Mather J P, Biol. Reprod. 23:243-252 (1980)); monkey kidney cell (CV1ATCC CCL 70); African green monkey kidney cell (VERO-76, ATCC CRL-1587); human cervical cancer cell (HELA, ATCC CCL 2); canine kidney cell (MDCK, ATCC CCL 34); Buffalo rat liver cell (BRL 3A, ATCC CRL 1442); human lung cell (W138, ATCC CCL75); human liver cell (Hep G2, HB 8065); mouse breast tumor (MMT 060562, ATCC CCL51); TRI cell (Mather et al., Annals NY Acad. Sci. 383: 44-68 (1982)); MRC 5 cell; FS4 cell; and human liver cancer cell line (HepG2). In certain preferred embodiments, the host cell is a 293F cell.

The host cell is introduced with the above-mentioned expression or cloning vector that can produce the antibody and antigen-binding fragment thereof, and it was cultured in a conventional nutrient medium, in which the nutrient medium is modified to be suitable for promoter induction and selective transformation of cell or amplification of gene encoding a target sequence.

The host cell used in the present application to produce the antibody and antigen-binding fragment thereof can be cultured in a variety of media well-known in the art. The medium may further contain any other necessary additives in appropriate concentrations known in the art. The conditions of the medium, such as temperature, pH and the like, are the conditions previously used for selecting host cells for expression, and are well known to those of ordinary skill.

When using recombinant technology, the antibody can be produced intracellularly, in the periplasmic space, or directly secreted into the culture medium. If the antibody is produced intracellularly, the particulate remains of the host cells or lysed fragments are first removed, for example, by centrifugation or ultrasound. Carter et al., Bio/Technology 10:163-167 (1992) describe a method for separating an antibody secreted into the periplasmic space of *E. coli*. Briefly, the cell paste is melted for more than 30 minutes in the presence of uranyl acetate (pH 3.5), EDTA and PMSF. Centrifugation is performed to remove cell debris. If the antibody is secreted into the culture medium, a commercially available protein concentration filter, such as Iamicon or Millipore Pellicon ultrafiltration unit, is usually first used to concentrate the supernatant of the expression system. In any of the foregoing steps, a protease inhibitor such as PMSF to inhibit protein degradation, and an antibiotic to prevent the growth of accidental contaminants can be added.

The antibody produced from the cells can be purified by a purification method, such as hydroxyapatite chromatography, gel electrophoresis, dialysis, DEAE-cellulose ion exchange chromatography column, ammonium sulfate precipitation, salting out, and affinity chromatography, in which affinity chromatography is the preferred purification technique. The type of the antibody and the presence of any immunoglobulin Fc domain in the antibody determine whether protein A is suitable as an affinity ligand. Protein A can be used to purify an antibody based on human γ1, γ2, or γ4 heavy chain (Lindmark et al., J. Immunol. Meth. 62:13 (1983)). Protein G is suitable for all murine isoforms and human γ3 (Guss et al., EMBO J. 5:1567 1575 (1986)). Agarose is the most commonly used affinity ligand attachment matrix, but other matrices can also be used. Mechanically stable substrates such as controlled pore glass or polystyrene can achieve faster flow rate and shorter processing time in comparison with agarose. If the antibody contains the CH3 domain, it can be purified with Bakerbond ABX™ resin (J. T. Baker, Phillipsburg, N.J.). Other protein purification techniques can also be determined according to the antibodies that need to be obtained, such as fractionation in ion exchange column, ethanol precipitation, reversed-phase HPLC, silica gel chromatography, heparin sepharose chromatography based on anion or cation exchange resins (for example, polyaspartate column), chromatographic focusing, SDS-PAGE, and ammonium sulfate precipitation.

After any preliminary purification steps, the mixture containing the antibody of interest and impurities can be treated by low pH hydrophobic interaction chromatography using an elution buffer with a pH of about 2.5 to 4.5, preferably at a low salt concentration (for example, a salt concentration from about 0 to 0.25M).

Pharmaceutical Composition and Therapeutic Use

In another aspect, the present application provides a pharmaceutical composition, which comprises the antibody or antigen-binding fragment thereof of the present application, the bispecific or multispecific molecule of the present application or the immunoconjugate of the present application, and a pharmaceutically acceptable carrier and/or excipient.

In certain embodiments, the pharmaceutical composition may also comprises an additional pharmaceutically active agent.

In certain embodiments, the additional pharmaceutically active agent is a drug with an anti-tumor activity, such as alkylating agent, mitotic inhibitor, anti-tumor antibiotic, antimetabolite, topoisomerase inhibitor, tyrosine kinase inhibitor, radionuclide agent, radiosensitizer, anti-angiogenesis agent, cytokine, molecular-targeted drug, immune checkpoint inhibitor or oncolytic virus.

In certain embodiments, the antibody or antigen-binding fragment thereof, bispecific or multispecific molecule or immunoconjugate and the additional pharmaceutically active agent are provided as separate components or as components of the same composition. The antibody or antigen-binding fragment thereof of the present application and the additional pharmaceutically active agent can be administered simultaneously, separately or sequentially.

The present application further provides a pharmaceutical composition comprising the antibody and one or several pharmaceutically acceptable carriers.

The pharmaceutically acceptable carrier used in the pharmaceutical composition disclosed in the present application may include, for example, a pharmaceutically acceptable liquid, gel or solid carrier, aqueous phase medium, non-aqueous phase medium, antimicrobial substance, isotonic substance, buffer, antioxidant, anesthetic, suspending agent/dispersant, integrating agent, diluent, adjuvant, excipient or non-toxic auxiliary substance, other components known in the art, or any combination of the above.

Suitable component may include, for example, antioxidant, filler, binder, disintegrant, buffer, preservative, lubricant, flavor, thickener, colorant, emulsifier or stabilizer such as sugar and cyclodextrin. Suitable antioxidant may include, for example, methionine, ascorbic acid, EDTA, sodium thiosulfate, platinum, catalase, citric acid, cysteine, mercaptoglycerol, thioglycolic acid, mercaptosorbitol, butylmethylanisole, butylated hydroxytoluene and/or propyl gallate. If one or several antioxidants such as methionine is present in a composition containing the antibody disclosed in the present application, the oxidation of the antibody may be reduced. The reduction in oxidation can prevent or reduce the decrease in binding affinity, thereby improving antibody stability and extending shelf life.

Furthermore, the pharmaceutically acceptable carrier may include, for example, aqueous medium such as sodium chloride injection, Ringer's solution injection, isotonic dextrose injection, sterile water injection, or glucose and lactate Ringer's injections, non-aqueous medium such as: plant-derived fixed oil, cotton seed oil, corn oil, sesame oil, or peanut oil, antibacterial substance at bacterial or fungal inhibitory concentration, isotonic agent such as sodium chloride or glucose, buffer such as phosphate or citrate buffer, antioxidant such as sodium bisulfate, local anesthetic such as procaine hydrochloride, suspending aid and dispersing agent such as sodium carboxymethylcellulose, hydroxypropylmethylcellulose or polyvinylpyrrolidone, emulsifier such as polysorbate 80 (Tween-80), integration reagent such as EDTA (ethylenediaminetetraacetic acid) or EGTA (ethylene glycol-bis(2-aminoethyl ether) tetraacetic acid), ethanol, polyethylene glycol, propylene glycol, sodium hydroxide, hydrochloric acid, citric acid or lactic acid. The antibacterial agent as a carrier can be added to the pharmaceutical composition in a multi-dose container, which includes phenols or cresols, mercury preparation, benzyl alcohol, chlorobutanol, methyl and propyl parabens, merthiolate, benzalkonium chloride, and triethylbenzonium chloride. Suitable excipient may include, for example, water, salt, glucose, glycerol or ethanol. Suitable non-toxic auxiliary substance may include, for example, emulsifier, pH buffer, stabilizer, solubilizer, or sodium acetate, sorbitan laurate, triethanolamine oleate or cyclodextrin.

The pharmaceutical composition can be a liquid solution, suspension, emulsion, pill, capsule, tablet, sustained release formulation or powder. Oral preparation may comprise standard carrier such as pharmaceutical grade mannitol, lactose, starch, magnesium stearate, polyvinylpyrrolidone, sodium saccharin, cellulose, magnesium carbonate and the like.

In certain embodiments, the pharmaceutical composition is formulated as a composition for injection. The pharmaceutical composition for injection can be prepared in any conventional form, for example, liquid solution, suspension, emulsion, or any solid form suitable for producing liquid solution, suspension, or emulsion. Injection preparation may comprise currently used sterile and/or pyrogen-free solution, sterile dry solvend that is combined with solvent before use, such as lyophilized powder, including subcutaneous tablet, sterile suspension ready for injection, sterile dry insoluble product that is combined with medium before use, and sterile and/or pyrogen-free emulsion. The solvent can be an aqueous phase or a non-aqueous phase.

In some embodiments, the unit-dose injection preparation is packaged in an ampoule, a tube, or a syringe with needle. It is known in the art that all preparations for injection administration should be sterile and pyrogen-free.

In some embodiments, a sterile lyophilized powder can be prepared by dissolving the antibody or antigen-binding fragment thereof disclosed in the present application in a suitable solvent. The solvent may contain a kind of other pharmacological component that can improve the stability of the powder or the reconstituted solution prepared from the powder, or improve the powder or the reconstituted solution. Suitable excipients include, but are not limited to, water, glucose, sorbitol, fructose, corn syrup, xylitol, glycerol, glucose, brown sugar or other applicable substances. The solvent may comprise a buffer, such as citrate buffer, sodium phosphate or potassium phosphate buffer, or other buffers known to those skilled in the art. In one embodiment, the pH of the buffer is neutral. The solution is subjected to subsequent filtration and sterilization under standard conditions known in the art, and then lyophilized to obtain an ideal formulation. In one embodiment, the resulting solvent is divided into small vials and lyophilized. Each vial may contain a single dose or multiple doses of the anti-CEACAM5 antibody or antigen-binding fragment thereof or combination thereof. The filling amount in each vial may be slightly higher than that required for each dose or multiple doses (for example, 10% overdose), so as to ensure accurate sampling and accurate administration. The lyophilized powder can be stored under appropriate conditions, such as in the range of about 4° C. to room temperature.

The lyophilized powder is re-dissolved with water for injection to obtain a preparation for injection administration. In one embodiment, the lyophilized powder can be reconstituted in sterile pyrogen-free water or other suitable liquid carrier. Its precise amount is determined by the selected therapy and can be determined based on empirical values.

Antibody Derivatization and Immunoconjugate

The antibody or antigen-binding fragment thereof of the present application can be derivatized, for example, linked to another molecule (for example, another polypeptide or protein). Generally, the derivatization (e.g., labeling) of the antibody or antigen-binding fragment thereof will not adversely affect its binding to CEACAM5. Therefore, the antibody or antigen-binding fragment thereof of the present application is also intended to comprise such derivatization forms. For example, the antibody or antigen-binding fragment thereof of the present application can be functionally linked (by chemical coupling, gene fusion, non-covalent linkage or other means) to one or several other molecular groups, such as another antibody (for example, to form a bispecific antibody), detection reagent, pharmaceutical reagent, and/or protein or polypeptide capable of mediating the binding of the antibody or antigen-binding fragment thereof to another molecule (for example, avidin or polyhistidine tag). In addition, the antibody or antigen-binding fragment thereof of the present application can also be derivatized with a chemical group, such as polyethylene glycol (PEG), methyl or ethyl, or glycosyl. These groups can be used to improve the biological properties of the antibody, such as increasing serum half-life.

Therefore, in one aspect, the present application provides an immunoconjugate, which comprises the antibody or antigen-binding fragment thereof described in the present application and a therapeutic agent conjugated to the antibody or antigen-binding fragment thereof.

In certain embodiments, the therapeutic agent is selected from cytotoxic agents.

In certain embodiments, the therapeutic agent is selected from alkylating agent, mitotic inhibitor, anti-tumor antibiotic, antimetabolite, topoisomerase inhibitor, tyrosine kinase inhibitor, radionuclide agent, and any combination thereof.

In certain embodiments, the immunoconjugate is an antibody-drug conjugate (ADC).

Kit and Detection Use

The antibody or antigen-binding fragment thereof of the present application can specifically bind to CEACAM5 protein, and basically does not bind to CEACAM1, CEACAM3, CEACAM7, CEACAM8 proteins, and only weakly binds to CEACAM6 protein. Therefore, the antibody or antigen-binding fragment thereof of the present application has higher specificity and accuracy in detection.

Therefore, in another aspect, the present application provides a kit, which comprises the antibody or antigen-binding fragment thereof of the present application, or the conjugate of the present application.

In some embodiments, the antibody or antigen-binding fragment thereof comprises a detectable label, such as an enzyme (for example, horseradish peroxidase), radionuclide, fluorescent dye, luminescent substance (for example, chemiluminescent substance), or biotin.

In some embodiments, the kit further comprises a second antibody, which specifically recognizes the antibody or antigen-binding fragment thereof.

In some embodiments, the second antibody further comprises a detectable label, such as an enzyme (for example, horseradish peroxidase), radionuclide, fluorescent dye, luminescent substance (for example, chemiluminescent substance), or biotin.

In some embodiments, the kit of the present application may further comprise a reagent for allowing the corresponding detectable label to be detected. For example, when the detectable label is an enzyme, the kit may also comprise a chromogenic substrate for the corresponding enzyme, such as o-phenylenediamine (OPD) for horseradish peroxidase, and tetramethylbenzidine (TMB), ABTS or luminol compound, or p-nitrophenyl phosphate (p-NPP) or AMPPD for alkaline phosphatase. For example, when the detectable label is a chemiluminescent reagent (for example, an acridine ester compound), the kit may further comprise a pre-excitation solution and/or an excitation solution for chemiluminescence.

In another aspect, the present application also provides a use of the antibody or antigen-binding fragment thereof in the manufacture of a kit, the kit is used for detecting whether a tumor can be treated by an anti-tumor therapy targeting CEACAM5.

In certain embodiments, the antibody or antigen-binding fragment thereof bears a detectable label.

In certain embodiments, the CEACAM5 is human CEACAM5.

In certain embodiments, the tumor is selected from the group consisting of non-small cell lung cancer, small cell lung cancer, renal cell carcinoma, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymic cancer, leukemia, lymphoma, myeloma, mycosis fungoids, Merkel cell cancer and other hematological malignancies, such as typical Hodgkin's lymphoma (CHL), primary mediastinal large B-cell lymphoma, T-cell/histiocytic B-cell-rich lymphoma, EBV-positive and negative PTLD and EBV-related diffuse large B-cell lymphoma (DLBCL), plasmablastic lymphoma, extranodal NK/T cell lymphoma, nasopharyngeal carcinoma and HHV8-related primary exudative lymphoma, Hodgkin's lymphoma, central nervous system (CNS) tumor, such as primary CNS lymphoma, spinal axis tumor, brainstem glioma.

The present application provides a kit comprising the antibody or antigen-binding fragment thereof. In some embodiments, the kit is used to detect the presence or level of CEACAM5 in a biological sample. The biological sample may comprise cells or tissues.

In some embodiments, the kit comprises an antibody or antigen-binding fragment thereof conjugated to a detectable label. In some embodiments, the kit comprises an unlabeled antibody, and further comprises a labeled secondary antibody capable of binding to the unlabeled antibody. The kit may further comprise an instruction for use, and a wrappage that separates each component in the kit.

In some embodiments, the antibody is linked to a substrate or an instrument for sandwich assays such as ELISA or immunochromatographic assays. Suitable substrate or instrument can be, for example, microplate and test paper.

Chimeric Antigen Receptor

In another aspect, the present application also provides a chimeric antigen receptor, which comprises an antigen-binding domain of the antibody or antigen-binding fragment thereof.

In certain embodiments, the antigen-binding domain comprises a heavy chain variable region and a light chain variable region of the antibody or antigen-binding fragment thereof.

In certain embodiments, the antigen-binding domain is a scFv.

In certain embodiments, the chimeric antigen receptor comprises the antigen-binding fragment of the antibody.

In certain embodiments, the chimeric antigen receptor is expressed by an immune effector cell (for example, T cell).

In another aspect, the present application also provides an isolated nucleic acid molecule, which encodes the chimeric antigen receptor.

In another aspect, the present application also provides a vector, which comprises the isolated nucleic acid molecule; in some embodiments, it is used to prepare a chimeric antigen receptor T cell.

In another aspect, the present application also provides a host cell, which comprises the isolated nucleic acid molecule or vector.

In certain embodiments, the host cell is an immune effector cell (for example, T cell or NK cell).

In certain embodiments, the host cell is a chimeric antigen receptor T cell (CAR-T).

Detection Method and Treatment Method

In many malignant tumors, the overexpression of CEACAM5 can be used as a tumor biomarker. Therefore, the measurement of CEACAM5 in the blood of patients can be used for the prognosis and control of cancer, and the targeted therapy of CEACAM5 has also become a potential cancer treatment method. The antibody of the present application (for example, UM05-5L and hUM05-3) can bind to CEACAM5 protein with high affinity and high specificity, and has ADCC activity, which can inhibit tumor growth and kill tumor cells.

Therefore, in another aspect, the present application also provides a method for inhibiting growth of a tumor cell expressing CEACAM5 and/or killing the tumor cell, which comprises contacting the tumor cell with an effective amount of the antibody or antigen-binding fragment thereof, or the bispecific or multispecific molecule, or the immunoconjugate, or the pharmaceutical composition, or the chimeric antigen receptor, or the host cell.

In another aspect, the present application also provides a method for reducing the expression level of CEACAM5 on the surface of a cell, which comprises contacting the tumor cell with an effective amount of the antibody or antigen-binding fragment thereof, or the bispecific or multispecific molecule, or the immunoconjugate, or the pharmaceutical composition, or the chimeric antigen receptor, or the host cell, so as to reduce the expression level of CEACAM5 on the cell surface; wherein, the cell expresses CEACAM5 on its surface.

In certain embodiments, the cell is a tumor cell expressing CEACAM5.

In another aspect, the present application also provides a method for preventing and/or treating a tumor in a subject (for example, a human), the method comprising administering to the subject in need thereof an effective amount of the antibody or antigen-binding fragment thereof, or the bispecific or multispecific molecule, or the immunoconjugate, or the pharmaceutical composition, or the chimeric antigen receptor, or the host cell.

In certain embodiments, the tumor expresses CEACAM5.

In certain embodiments, the tumor involves a tumor cell that expresses CEACAM5. In certain embodiments, the CEACAM5 is expressed on the surface of the tumor cell.

In certain embodiments, the tumor is selected from the group consisting of non-small cell lung cancer, small cell lung cancer, renal cell carcinoma, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymic cancer, leukemia, lymphoma, myeloma, mycosis fungoids, Merkel cell cancer and other hematological malignancies, such as typical Hodgkin's lymphoma (CHL), primary mediastinal large B-cell lymphoma, T cell/histiocytic rich B cell lymphoma, EBV-positive and negative PTLD and EBV-related diffuse large B-cell lymphoma (DLBCL), plasmablastic lymphoma, extranodal NK/T-cell lymphoma, nasopharyngeal carcinoma, and HHV8-related primary exudative lymphoma, Hodgkin's lymphoma, central nervous system (CNS) tumor, such as primary CNS lymphoma, spinal axis tumor, brainstem glioma.

In certain embodiments, the subject is a mammal, such as a human.

In certain embodiments, the method further comprises administering an additional drug with an anti-tumor activity, such as alkylating agent, mitotic inhibitor, anti-tumor antibiotic, antimetabolite, topoisomerase inhibitor, tyrosine kinase inhibitor, radionuclide agent, radiosensitizer, anti-angiogenesis agent, cytokine, molecular targeted drug, immune checkpoint inhibitor or oncolytic virus.

In certain embodiments, the method further comprises administering an additional anti-tumor therapy, such as surgery, chemotherapy, radiation therapy, targeted therapy, immunotherapy, hormone therapy, gene therapy, or palliative therapy.

In another aspect, the present application also provides a use of the antibody or antigen-binding fragment thereof, or the bispecific or multispecific molecule, or the immunoconjugate, or the pharmaceutical composition, or the chimeric antigen receptor, or the host cell, in the manufacture of a medicament for the prevention and/treatment of a tumor in a subject (for example, a human).

In certain embodiments, the medicament further comprises an additional pharmaceutically active agent.

In certain embodiments, the additional pharmaceutically active agent is a drug with anti-tumor activity, such as alkylating agent, mitotic inhibitor, anti-tumor antibiotic, antimetabolite, topoisomerase inhibitor, tyrosine kinase inhibitor, radionuclide agent, radiosensitizer, anti-angiogenesis agent, cytokine, molecular targeted drug, immune checkpoint inhibitor or oncolytic virus.

In certain embodiments, the tumor expresses CEACAM5.

In certain embodiments, the tumor involves a tumor cell that expresses CEACAM5; preferably, the CEACAM5 is expressed on the surface of the tumor cell.

In certain embodiments, the tumor is selected from the group consisting of non-small cell lung cancer, small cell lung cancer, renal cell carcinoma, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymic cancer, leukemia, lymphoma, myeloma, mycosis fungoids, Merkel cell cancer and other hematological malignancies, such as typical Hodgkin's lymphoma (CHL), primary mediastinal large B-cell lymphoma, T-cell/histiocytic B-cell-rich lymphoma, EBV-positive and negative PTLD and EBV-related diffuse large B-cell lymphoma (DLBCL), plasmablastic lymphoma, extranodal NK/T cell lymphoma, nasopharyngeal carcinoma and HHV8-related primary exudative lymphoma, Hodgkin's lymphoma, central nervous system (CNS) tumor, such as primary CNS lymphoma, spinal axis tumor, brainstem glioma.

In certain embodiments, the subject is a mammal, such as a human.

In another aspect, the present application also provides a method for detecting the presence or amount of CEACAM5 (for example, human CEACAM5) in a sample, which comprises the following steps:

(1) contacting the sample with the antibody or antigen-binding fragment thereof;

(2) detecting formation of a complex comprising the antibody or antigen-binding fragment thereof and CEACAM5, or detecting an amount of the complex.

In certain embodiments, the antibody or antigen-binding fragment thereof comprises a detectable label.

In certain embodiments, the CEACAM5 is human CEACAM5.

In another aspect, the present application also provides a method for determining whether a tumor can be treated by an anti-tumor therapy targeting CEACAM5, which comprises the following steps:

(1) contacting a sample containing a cell of the tumor with the antibody or antigen-binding fragment thereof;

(2) detecting formation of a complex comprising the antibody or antigen-binding fragment thereof and CEACAM5.

In certain embodiments, the antibody or antigen-binding fragment thereof bears a detectable label.

In certain embodiments, the CEACAM5 is human CEACAM5.

In certain embodiments, the tumor is selected from the group consisting of non-small cell lung cancer, small cell lung cancer, renal cell carcinoma, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymic cancer, leukemia, lymphoma, myeloma, mycosis fungoids, Merkel cell cancer and other hematological malignancies, such as typical Hodgkin's lymphoma (CHL), primary mediastinal large B-cell lymphoma, T-cell/histiocytic B-cell-rich lymphoma, EBV-positive and negative PTLD and EBV-related diffuse large B-cell lymphoma (DLBCL), plasmablastic lymphoma, extranodal NK/T cell lymphoma, nasopharyngeal carcinoma and HHV8-related primary exudative lymphoma, Hodgkin's lymphoma, central nervous system (CNS) tumor, such as primary CNS lymphoma, spinal axis tumor, brainstem glioma.

The present application also provides a therapeutic method, comprising administering a therapeutically effective amount of the antibody described in the present application to a subject in need thereof.

The therapeutically effective amount of the antibody provided in the present application depends on a variety of factors known in the art, such as weight, age, past medical history, current treatment, subject's health status and cross-infection potential, allergies, hypersensitivity and side effect, and administration route and tumor development degree. Those skilled in the art (for example, doctors or veterinarians) can reduce or increase the amount in proportion according to these or other conditions or requirements.

In certain embodiments, the antibody provided in the present application can be administered at a therapeutically effective dose between about 0.01 mg/kg and about 100 mg/kg. In some embodiments, the antibody is administered at a dose of about 50 mg/kg or less. In some embodiments, the administration dose is 10 mg/kg or less, 5 mg/kg or less, 1 mg/kg or less, 0.5 mg/kg or less, or 0.1 mg/kg or less. A specific dose can be administered at multiple intervals, such as once per day, twice or more per day, twice or more per month, once per week, once every two weeks, once every three weeks, once per month, or once every two or more months. In certain embodiments, the administration dose can vary with the course of treatment. For example, in certain embodiments, the initial administration dose may be higher than the subsequent administration dose. In some embodiments, the administration dose is adjusted according to the subject's response to the administration during the course of treatment.

The dosage regimen can be adjusted to achieve the optimal response (for example, treatment response). For example, the administration can be performed in a single dose or in multiple divided doses over a period of time.

The antibody disclosed in the present application can be administered by a method known in the art, such as injection administration (for example, subcutaneous injection, intraperitoneal injection, intravenous injection, including intravenous drip, intramuscular injection or intradermal injection) or non-injection administration (for example, oral administration, nasal administration, sublingual administration, rectal administration, or topical administration).

In certain embodiments, the antibody can be used for the treatment of a disease associated with its molecular mechanism, including tumor and cancer, such as non-small cell lung cancer, small cell lung cancer, renal cell carcinoma, colorectal cancer, ovarian cancer, breast cancer, pancreas cancer, stomach cancer, bladder cancer, esophageal cancer, mesothelioma, melanoma, head and neck cancer, thyroid cancer, sarcoma, prostate cancer, glioblastoma, cervical cancer, thymic cancer, leukemia, lymphoma, myeloma, mycosis fungoids, Merkel cell carcinoma and other hematological malignancies, such as typical Hodgkin's lymphoma (CHL), primary mediastinal large B-cell lymphoma, T cell/histiocytic B-cell lymphoma, EBV-positive and negative PTLD and EBV-related diffuse large B-cell lymphoma (DLBCL), plasmablastic lymphoma, extranodal NK/T-cell lymphoma, nasopharyngeal carcinoma and HHV8-related primary exudative lymphoma, Hodgkin's lymphoma, central nervous system (CNS) tumor, such as primary CNS lymphoma, spinal axis tumor, brainstem glioma.

Usage

The present application further provides a method for using the antibody.

In some embodiments, the present application provides a method of treating a condition or disease related to a mechanism of the antibody in an individual, comprising administering a therapeutically effective amount of the antibody described herein.

The antibody disclosed in the present application can be administered alone or in combination with one or several other therapeutic means or substances. For example, the antibody disclosed in the present application can be used in combination with chemotherapy, radiotherapy, cancer treatment surgery (for example, tumor resection), antiviral drug, one or several antiemetic drugs or other therapies for chemotherapy-induced complication, or any other therapeutic substances for cancer or virus. In some such embodiments, when the antibody disclosed in the present application is used in combination with one or several therapeutic substances, it can be administered simultaneously with the one or several therapeutic substances. In some such embodiments, the antibody can be administered simultaneously as part of the same pharmaceutical composition. However, antibody that is "used in combination" with another therapeutic substance does not need to be administered at the same time or in the same composition with the therapeutic substance. The meaning of "used in combination" in the present application also comprises that an antibody administered before or after another therapeutic substance is also considered to be "used in combination" with the therapeutic substance, even if the antibody and the second substance are administered in different ways. Where possible, other therapeutic substances used in combination with the antibody disclosed in the present application can be administered by referring to the r product instructions of the other therapeutic substances, or refer to the surgeon's desk reference 2003 (Physicians' Desk Reference, 57th Ed; Medical Economics Company; ISBN: 1563634457; 57th edition (November 2002)), or refer to other methods known in the art.

In some embodiments, the therapeutic substance can induce or enhance an immune response against a cancer. For example, a tumor vaccine can be used to induce an immune response to a certain tumor or cancer. Cytokine therapy can be used to increase the presentation of a tumor antigen to the immune system. Examples of cytokine therapy include but are not limited to interferon such as interferon α, β and γ, colony stimulating factor such as macrophage CSF, granulocyte macrophage CSF and granulocyte CSF, and interleukin such as IL-1, IL-1a, IL-2, IL-3, IL-4, IL-5, IL-6, IL-7, IL-8, IL-9, IL-10, IL-11 and IL-12, tumor necrosis factor such as TNF-α and TNF-β. Reagents that inactivate immunosuppressive targets can also be used, and the examples include PD-1 antibody, TGF-β inhibitor, IL-10 inhibitor, and Fas ligand inhibitor. Another group of reagents includes those that activate an immune response to a tumor or cancer cell, for example, those that increase T cell activation (for example, T cell costimulatory signaling pathway, for example pathway such as CTLA-4, ICOS, OX40, 4-1BB, etc.), and those that improve dendritic cell function and antigen presentation.

The following examples are intended to better illustrate the present application, and should not be construed as limiting the scope of the present application. All of the following specific compositions, materials and methods, in whole or in part, are within the scope of the present application. These specific compositions, materials and methods are not intended to limit the present application, but only to illustrate specific embodiments within the scope of the present application. Those skilled in the art can develop equivalent compositions, materials and methods without adding creativity and without departing from the scope of the present application. It should be understood that various changes made to the method of the present application may still fall into the scope of the present application. The present inventors intend to include such changes within the scope of the present application.

Sequence Information

The information of some sequences involved in the present application is shown in Table 1 below.

TABLE 1

Information of some sequences

| SEQ ID NO: | Sequence description | Sequence information |
|---|---|---|
| 1 | UM05-5L VH CDR1 | DHTIH |
| 2 | UM05-5L VH CDR2 | YIYPRDGNTKYNEKFKG |
| 3 | UM05-5L VH CDR3 | PIYDGYSFDY |
| 4 | UM05-5L VL CDR1 | RASSSVSYMH |
| 5 | UM05-5L VL CDR2 | DTSKLAS |
| 6 | UM05-5L VL CDR3 | QQWTRNPPT |

TABLE 1-continued

Information of some sequences

| SEQ ID NO: | Sequence description | Sequence information |
|---|---|---|
| 7 | UM05-5L VH | QVQLQQSDADLVKPGASVKISCKVSGYTFTDHTIHWMKQRPEQGLECIGYIYPRDGNTKYNEKFKGKATLTADRSSITAYMQLNSLTSEDSAVYFCARPIYDGYSFDYWGQGTTLTVSS |
| 8 | UM05-5L VL | QIVLTQSPAIMSASPGEKVTMTCRASSSVSYMHWYQQKSGTSPKRWIYDTSKLASGVPARFSGSGSGTSYSLTISSMAAEDAATYYCQQWTRNPPTFGAGTKLELK |
| 9 | IgG1 heavy chain constant region | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 10 | Nucleotide sequence encoding IgG1 heavy chain constant region | GCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCCGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAATGA |
| 11 | κ chain constant region | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 12 | Nucleotide sequence encoding κ chain constant region | CGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGTTCGCCCGTCACAAAGAGCTTCAACAGGGGAGAGTGTTGA |
| 13 | VH-G4S3-VL | QVQLQQSDADLVKPGASVKISCKVSGYTFTDHTIHWMKQRPEQGLECIGYIYPRDGNTKYNEKFKGKATLTADRSSITAYMQLNSLTSEDSAVYFCARPIYDGYSFDYWGQGTTLTVSSGGGGSGGGGSGGGGSQIVLTQSPAIMSASPGEKVTMTCRASSSVSYMHWYQQKSGTSPKRWIYDTSKLASGVPARFSGSGSGTSYSLTISSMAAEDAATYYCQQWTRNPPTFGAGTKLELK |
| 14 | UM05-5L VH gene | CAGGTTCAGCTGCAACAGTCTGACGCTGACTTGGTGAAACCTGGAGCTTCAGTGAAGATATCCTGCAAGGTCTCTGGCTACACCTTCACTGACCATACTATTCACTGGATGAAGCAGAGGCCTGAACAGGGCCTGGAATGCATTGGATATATTTATCCTAGAGATGGTAATACTAAGTACAATGAGAAGTTCAAGGGCAAGGCCACATTGACTGCAGACAGATCCTCCATCACAGCCTACATGCAGCTCAACAGCCTGACATCTGAGGACTCTGCAGTCTATTTCTGTGCAAGACCCATCTATGATGGTTACTCCTTTGACTACTGGGGCCAAGGCACCACTCTCACAGTCTCCTCA |
| 15 | UM05-5L VL gene | CAAATTGTTCTCACCCAGTCTCCAGCAATCATGTCTGCATCTCCAGGGGAGAAGGTCACCATGACCTGCCGTGCCAGCTCAAGTGTTAGTTACATGCACTGGTACCAGCAGAAGTCAGGCACCTCCCCCAAAAGATGGATTTATGACACATCCAAACTGGCTTCTGGAGTCCCTGCTCGCTTCAGTGGCAGTGGGTCTGGGACCTCTTACTCTCTCACAATCAGCAGCATGGCGGCTGAAGATGCTGCCACTTATTACTGCCAGCAGTGGACTCGTAACCCACCTACCTTCGGTGCTGGGACCAAGCTGGAGCTGAAA |

TABLE 1-continued

| Information of some sequences | | |
|---|---|---|
| SEQ ID NO: | Sequence description | Sequence information |
| 16 | hUM05-3 VH | EVQLVQSGAEVKKPGATVKISCKVSGYTFTDHTMHWMQQAPGQGLEWIGLI YPRDGSTIYNEKFQGRATLTADRSTDTAYMELSSLRSEDTAVYFCARPIYDG YSFDYWGQGTLVTVSS |
| 17 | hUM05-3 VL | QIVLTQSPATLSASPGERATLSCRASSSVSYMHWYQQKPGQAPKRWIYDTSN RATGVPARFSGSGSGTDYTLTISSMEPEDAAVYYCQQWTRNPPTFGQGTKLE LK |
| 18 | UM05-5L C47W VH | QVQLQQSDADLVKPGASVKISCKVSGYTFTDHTIHWMKQRPEQGLEWIGYI YPRDGNTKYNEKFKGKATLTADRSSITAYMQLNSLTSEDSAVYFCARPIYDG YSFDYWGQGTTLTVSS |
| 19 | hUM05-3 W47C VH | EVQLVQSGAEVKKPGATVKISCKVSGYTFTDHTMHWMQQAPGQGLECIGLI YPRDGSTIYNEKFQGRATLTADRSTDTAYMELSSLRSEDTAVYFCARPIYDG YSFDYWGQGTLVTVSS |
| 20 | hUM05-3 VH CDR1 | DHTMH |
| 21 | hUM05-3 VH CDR2 | LIYPRDGSTIYNEKFQG |
| 22 | hUM05-3 VL CDR2 | DTSNRAT |

Beneficial Effect

The monoclonal antibody of the present application (for example, UM05-5L, hUM05-3 antibody) can bind to CEACAM5 protein or a cell expressing CEACAM5 protein with high specificity and selectivity, and it does not substantially bind to CEACAM1, CEACAM3, CEACAM7, CEACAM8 proteins, and only weakly binds with CEACAM6 protein. At the same time, the antibody UM05-5L also has ADCC activity. The UM05-5L-CAR constructed based on the antibody UM05-5L can be expressed on the surface of a human T cell, can recognize a tumor cell in vivo, secrete cytokine, and has a strong tumor-inhibiting effect. Therefore, the monoclonal antibody of the present application (for example, UM05-5L, hUM05-3 antibody) has high clinical application value.

SPECIFIC MODELS FOR CARRYING OUT THE INVENTION

The present application will now be described with reference to the following examples which are intended to illustrate the present application (not limit the present application).

Unless otherwise specified, the molecular biology experimental methods and immunoassay methods used in the present application basically referred to J. Sambrook et al., Molecular Cloning: Laboratory Manual, 2nd Edition, Cold Spring Harbor Laboratory Press, 1989, and F M Ausubel et al., Compiled Molecular Biology Experiment Guide, 3rd edition, John Wiley & Sons, Inc., 1995; the restriction enzymes were used in accordance with the conditions recommended by the product manufacturer. If specific conditions were not indicated in the examples, it should be carried out in accordance with the conventional conditions or the conditions recommended by the manufacturer. The reagents or instruments used without the manufacturer's indication were all conventional products that were purchased commercially. Those skilled in the art know that the examples describe the present application by way of example, and are not intended to limit the scope of protection claimed by the present application.

Example 1

Acquisition of Monoclonal Antibody Against Human CEACAM5 Protein

Figure 1:
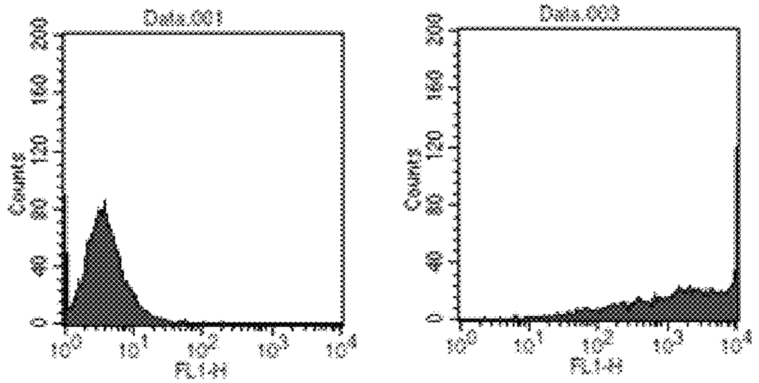
FIG. 1 showed the expression level of CEACAM5 in the CHO cell line constructed in the present application; as compared with conventional CHO cells, the expression level of CEACAM5 in the CHO cell line constructed in the present application was up to 904 times.

In the present application, a CHO cell line overexpressing CEACAM5 protein was constructed. In short, the CEACAM5 plasmid (Beijing Yiqiao Shenzhou Technology Co., Ltd., HG11077-UT) was transfected into a CHO cell line (ATCC) and expressed. The plasmid was resistant to hygromycin (Hygromycin), so that a cell stably transfected with this plasmid could be stably passaged in a medium containing hygromycin. The cells were picked and the expression of CEACAM5 was measured. As shown in FIG. 1, the CHO-CEACAM5 cell showed a 904-times increased CEACAM5 expression, as detected by FACS.

The CHO-CEACAM5 cells and the CEACAM5 protein (L2C01001) purified from tumor patients were used to immunize 6 Balb/c mice aged 5-8 weeks (Shanghai Slack) according to the immunization schedule in Table 2.

TABLE 2

Immunization schedule in mice

| Date | Operation | Antigen | Adjuvant |
|---|---|---|---|
| Day 1 | Immunization by intraperitoneal injection | CHO-CEACAM5 cells | CFA |
| Day 26 | Immunization by intraperitoneal injection | CHO-CEACAM5 cells | IFA |
| Day 49 | Immunization by intraperitoneal injection | CHO-CEACAM5 cells | IFA |
| Day 91 | Immunization by intraperitoneal injection | CEACAM5 protein | Gerbu (MM3001) |
| Day 104 | Immunization by intraperitoneal injection | CEACAM5 protein | Gerbu (MM3001) |
| Day 105 | Immunization by intraperitoneal injection | CEACAM5 protein | Gerbu (MM3001) |
| Day 106 | Immunization by intraperitoneal injection | CEACAM5 protein | Gerbu (MM3001) |

On the second day after the immunization, the spleen cells of the immunized mice were taken, and fused with SP2/0-AG14 cells (ATCC) to prepare hybridoma cells, and an appropriate amount of the fused cells were plated on a 96-well plate. About 10 days after the fusion, the supernatant of each well was taken, and the binding activity of the mouse antibody secreted by the hybridoma cells to human CEACAM5 was detected by ELISA.

Furthermore, supernatant from the well detected with strong positive ELISA signal was taken, its binding activity to LOVO cells (Shanghai Institute of Cell Biology, Chinese Academy of Sciences) was detected by flow cytometry, and hybridoma cells with high binding activity to LOVO cells were obtained. These cells were subcloned to obtain monoclonal cells. Table 3 showed the detection data of some hybridoma cells.

TABLE 3

Binding results of hybridoma cells to CEACAM

| Hybridoma cells | ELISA OD value | LOVO FACS binding |
|---|---|---|
| 1-2C5 | 1.0690 | 12.1 |
| 1-9G3 | 1.0390 | 7.01 |
| 3-2F3 | 1.4480 | 11 |
| 3-6F5 | 1.3520 | 6.51 |
| 3-8C10 | 2.3030 | 137 |
| 3-8G8 | 1.9270 | 82.9 |
| 2A10A5 | 2.392 | / |
| 2A10C4 | 2.434 | / |

The hybridoma cell 3-8C10 with better binding activity was selected for sequencing. After sequencing, an antibody was obtained, named UM05-5, and the CDR sequences of the UM05-5 antibody were determined by using the Kabat numbering system (Kabat et al., Sequences of Proteins of Immunological Interest, fifth edition, Public Health Service, National Institutes of Health, Bethesda, Maryland (1991), pages 647-669), and shown in Table 4.

TABLE 4

UM05-5 variable region sequences

| | SEQ ID NO: | | | | | | | | | |
|---|---|---|---|---|---|---|---|---|---|---|
| Monoclonal antibody | VH | VL | Numbering system | HCDR1 | HCDR2 | HCDR3 | LCDR1 | LCDR2 | LCDR3 |
| UM05-5 | 7 | 8 | Kabat | 1 | 2 | 3 | 4 | 5 | 6 |

Example 2

Preparation of Human-Mouse Chimeric Antibody

According to the sequence of UM05-5 in Table 4, a human-mouse chimeric antibody was designed and expressed, and named as UM05-5L. In short, the sequences encoding the mouse antibody VH and VL were respectively linked to the sequence encoding the human IgG1 heavy chain constant region (its amino acid sequence was shown in SEQ ID NO: 9, and its nucleotide sequence was shown in SEQ ID NO: 10) and the κ chain constant region sequence (its amino acid sequence was shown in SEQ ID NO: 11, and its nucleotide sequence was shown in SEQ ID NO: 12) to obtain the human-mouse chimeric antibody UM05-5L.

The nucleotide sequences encoding the heavy chain and light chain of the antibody were cloned into the mammalian cell expression vector pcDNA3.4, respectively. The heavy chain expression vector and light chain expression vector were transfected into HEK293 cells with Lipofectamine 2000 transfection reagent (Invitrogen) at a molar ratio of 2:1, and cultured at 37° C. and 5% carbon dioxide for 7 days. The culture medium supernatant was collected, and the antibody in the supernatant was purified by Protein A affinity chromatography. After the purification, the antibody was dialyzed with PBS solution, freeze-dried and concentrated, and stored at −20° C.

Example 3

Binding of Antibody to CEACAM5 Protein

Figure 2:
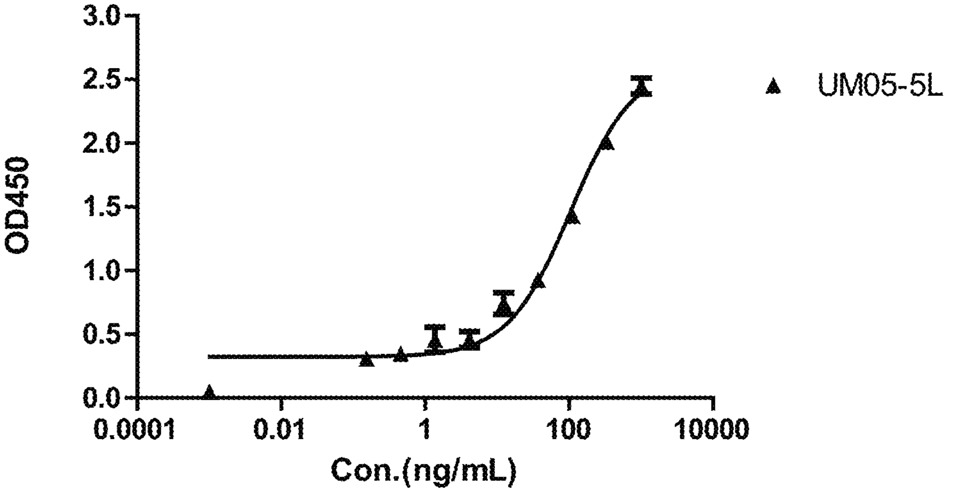
FIG. 2 showed the binding result between the antibody UM05-5L and CEACAM5 protein in an ELISA experiment.

A 96-well high-affinity plate was coated with a human CEACAM5 protein solution with a concentration of 1 μg/mL, 100 μL/well at 4° C., and shaken overnight. On the next day, it was first washed with 300 μL of PBST (Tween20: 0.5%) for 3 times, then blocked with 100 μL/well of 5% BSA/PBS for 1 hour, and shaken at room temperature. Washing was performed 3 times with 300 μL of PBST. A series of dilution solutions of antibody samples were prepared with PBS, and added at 100 μL/well to the 96-well plate and shaken at room temperature for 1 hour. Washing was performed 3 times with 300 μL of PBST. A secondary antibody goat anti-human IgG HRP solution was prepared, added at 100 μL/well to the 96-well plate, and shaken at room temperature for 30 minutes. Washing was performed 4 times with 300 μL of PBST. 100 μL/well TMB was added to perform color development for 20 min. 100 μL/well of 0.6N $H_2SO_4$ was added to stop the color development, and OD450 nm was detected. After detection, the results were shown in FIG. 2. The EC50 of the binding of the chimeric antibody UM05-5L to CEACAM5 protein was 105.3 ng/mL.

Example 4

Binding of Antibody to Cells Expressing CEACAM5

Flow cytometry (FACS) was used to detect the binding of antibody to LOVO tumor cells naturally expressing human CEACAM5 or cells overexpressing different CEACAM family members. In short, cells were first collected, washed with PBS, counted, and diluted to obtain $2*10^6$/ml cell suspension; 10 μl of an antibody working solution was added to 100 μl of the cell suspension, and incubated at 4° C. for 30 min in the dark; after washing twice with PBS, a corresponding fluorescent-labeled secondary antibody Goat-anti-Human IgG (H+L) (Invitrogen) was added, incubated at 4° C. for 30 min in the dark, after washing twice with PBS, it was suspended in 400 μl of FACS buffer, and the binding profile of the antibody to the cells were detected by FACS.

The binding profile of the supernatants of the chimeric antibody UM05-5L and the control antibody UM05-8 (anti-CEACAM5 antibody, prepared by the hybridoma method in our laboratory) to different cells at a concentration of 3 μg/mL were detected, in which SW620-CEACAM1 was a cell overexpressing CEACAM1, SW620-CEACAM3 was a cell overexpressing CEACAM3, CHO-CEACAM6 was a cell overexpressing CEACAM6, CHO-CEACAM7 was a cell overexpressing CEACAM7, and CHO-CEACAM8 was a cell overexpressing CEACAM8. The binding value (that was, the detection value of FACS) of the antibody to LOVO cells (which expressed CEACEM5) was normalized to 100%, and the relative binding activity of the antibody to different cells (which expressed different CEACAM proteins) were calculated, and the results were shown in Table 5.

TABLE 5

Binding of antibodies to LOVO cells and cells overexpressing different CEACAM proteins

| Cell name | UM05-5L | UM05-8 |
|---|---|---|
| LOVO | 100.00% | 100.00% |
| SW620-CEACAM1 | 2.01% | 120.47% |
| SW620-CEACAM3 | 1.29% | 91.56% |
| CHO-CEACAM6 | 26.60% | 69.61% |
| CHO-CEACAM7 | 0.38% | 13.71% |
| CHO-CEACAM8 | 0.40% | 61.60% |

It could be seen from Table 5 that the chimeric antibody UM05-5L had particularly outstanding selectivity: it bound to CEACAM5 with high affinity, but did not obviously bind to CEACAM1, CEACAM3, CEACAM7, CEACAM8 and only weakly bound to CEACAM6. While the ordinary antibody (for example, the control antibody UM05-8) could bind to CEACAM5, and simultaneously bind to CEACAM1, CEACAM3, CEACAM6, CEACAM7 and CEACAM8 at a higher level, and showed no selectivity.

Figure 3:
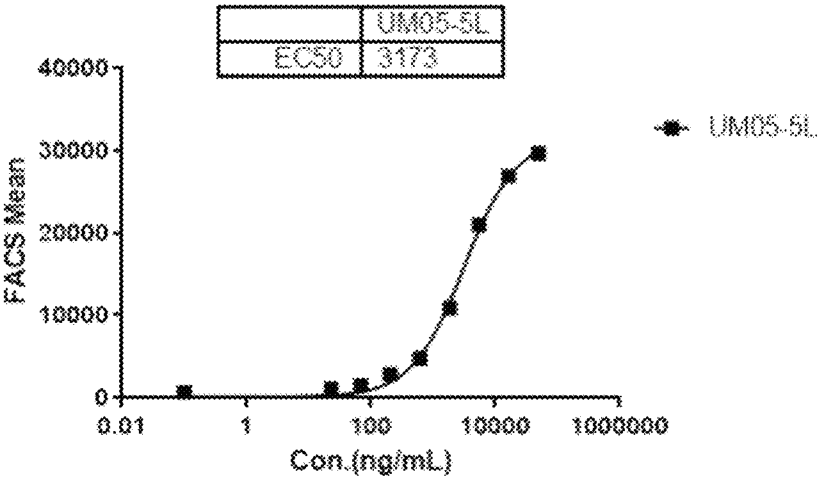
FIG. 3 showed the binding profile of the antibody UM05-5L to LOVO cells.

Furthermore, we used FACS to detect the EC50 of the chimeric antibody UM05-5L binding to LOVO tumor cells that naturally expressed human CEACAM5. The results were shown in FIG. 3, in which the EC50 of the chimeric antibody UM05-5L binding to LOVO cells was 3173 ng/mL. Based on the above results, the chimeric antibody UM05-5L had excellent binding affinity, specificity and selectivity to CEACAM5.

Example 5

ADCC Activity of Antibodies

Figure 4A:
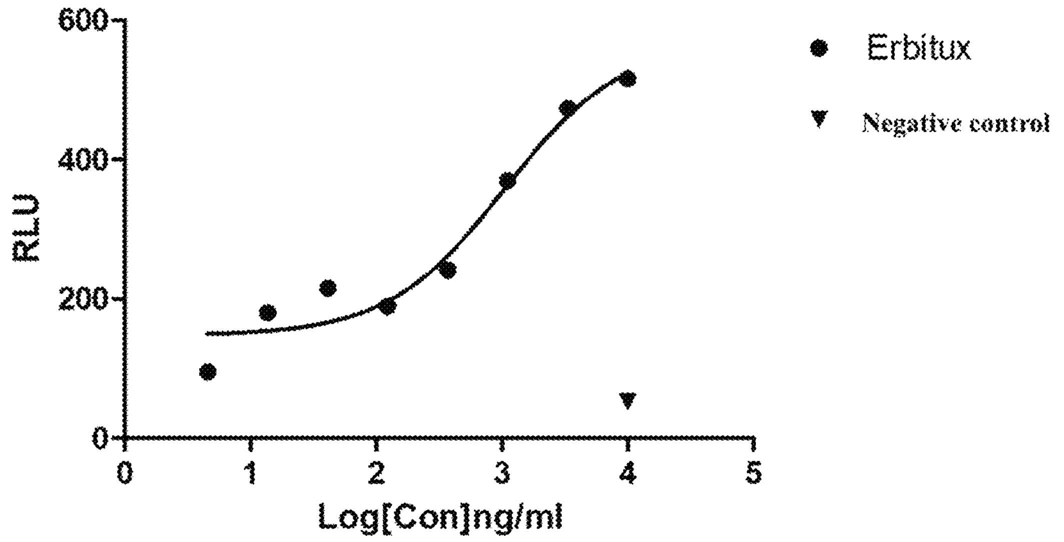
FIGS. 4*a* to 4*b* showed the ADCC activity of the antibody UM05-5L in a reporter cell line; in which, FIG. 4*a* showed the ADCC activity of the positive control (Erbitux antibody) and the negative control, and FIG. 4*b* showed the ADCC activity of UM05-5L.
Figure 4B:
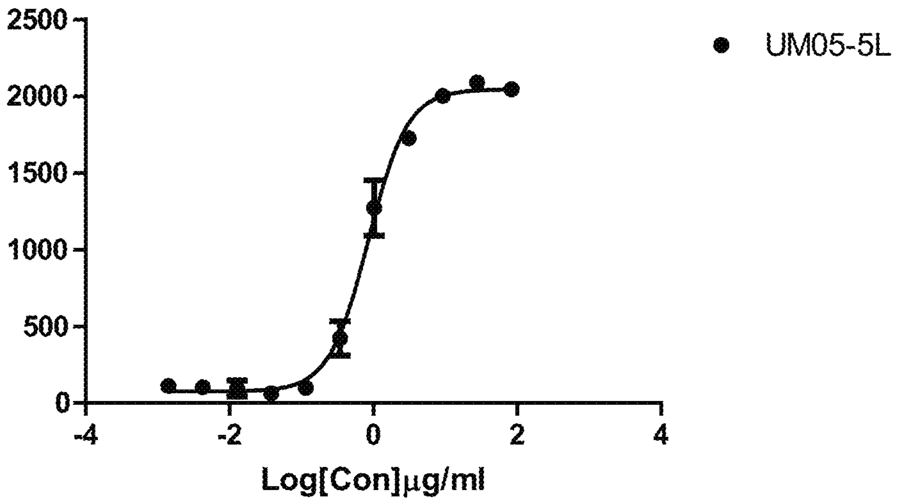

Using LOVO cells as target cells, the LOVO cells were inoculated on a 96-well cell culture plate at a density of 20,000 cells/well, and incubated overnight at 37° C. and 5% $CO_2$. On the second day, the antibody UM05-5L and the positive control antibody Erbitux were prepared at 20 μg/ml in the culture medium, and were diluted by 3 times to obtain 8 concentrations. The supernatant medium of the LOVO cells was removed by pipetting, and an antibody (positive control antibody Erbitux, chimeric antibody UM05-5L or negative control irrelevant antibody) with diluted to a specified concentration was added at 30 μL/well to the LOVO cells. Subsequently, effector cells Jurkat/ADC (Nanjing Nuoaixin Biotechnology Co., Ltd.) were plated into LOVO cell wells at 120,000 cells/30 μL/well, and incubated at 37° C. and 5% $CO_2$ for 16 to 20 hours. After the incubation, Bright-Glo kit (Promega, cat.E2620) was used to detect the expression level of luciferase in the effector cells. The luciferase level represented the degree of ADCC activation of the effector cells. FIG. 4*a* showed the ADCC activity of the positive control Erbitux antibody and the negative control, and FIG. 4*b* showed the ADCC activity of UM05-5L. Based on the above results, it could be seen that UM05-5L had strong ADCC activity with an EC50 of 0.85 μg/mL.

Example 6

Construction of CAR-T Cells Targeting CEACAM5

Based on the CAR-T structures of the second and third generations, we used anti-CEACAM5 single-chain antibody as CAR-T recognition antibody, and used one or several costimulatory components such as 41BB, CD28, OX40 and others to carry out the design of different CEA-CAR structures, and constructed corresponding lentiviral plasmids to generate lentivirus that could infect cells and express the corresponding CAR. The lentivirus could be used to infect T cells isolated from the peripheral blood of tumor patients, and produce CAR-T cells expressing corresponding CAR receptors on the cell membrane surface. This kind of CAR-T cells could effectively recognize and kill tumor cells expressing CEACAM5. In both in vitro and in vivo experiments, this cellular immunotherapy showed very good safety and efficacy.

The single chain antibody UM05-5L scFv (in the order of VH-G4S3-VL) as shown in SEQ ID NO: 13 was ligated to the sequence CD8α-CD137-CD3ζ-p2A-tEGFR to construct a chimeric antigen receptor CAR, and then the nucleotide sequence encoding the CAR was cloned into a lentiviral vector (Jike Gene, GV401), and the vector was named UM05-5L-CAR. The expression cassette was EF 1 a promoter-CAR-2A-tEGFR-WPRE.

The UM05-5L-CAR lentiviral vector and packaging plasmid were transiently transfected into 293T cells for 16 hours, the medium was changed, and the culture was continued for 24 to 48 hours. The supernatant (containing the lentivirus) was collected and stored at −80° C.

Figure 5A:
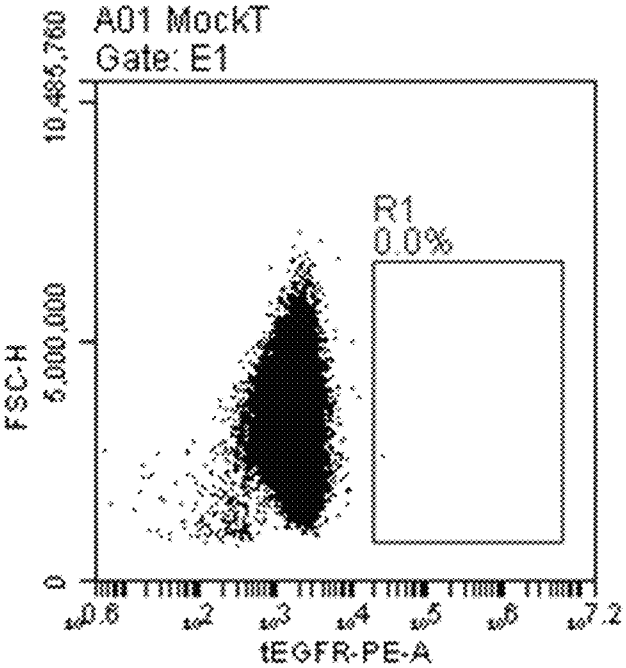
FIGS. 5*a* to 5*b* showed the results of flow cytometry; in which FIG. 5*a* showed the expression efficiency of control T cells (Mock T), and FIG. 5*b* showed the expression efficiency of UM05-5L-CAR.
Figure 5B:
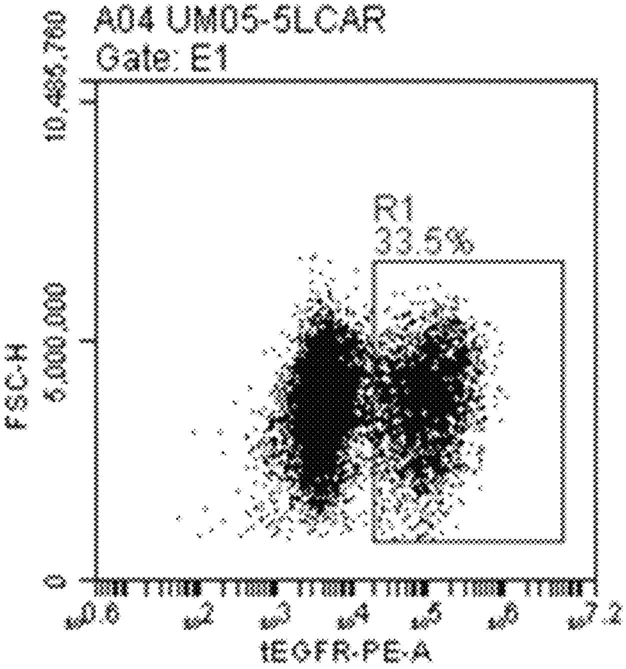

PBMC cells derived from healthy people were activated with CD3/28 antibody for 24 hours; the lentivirus and T cells were mixed according to MOI=3:1 and cultured for 96 hours, and the expression of UM05-5L-CAR was detected with PE fluorescent-labeled Cetuximab. The results were shown in FIG. 5. As compared to the control (FIG. 5*a*), UM05-5L-CAR (FIG. 5*b*) could be well expressed on the surface of human T cells.

Example 7

Functional Assessment of CAR-T Cells Targeting CEACAM5

1. Detection of Cytokine Release

Figure 6:
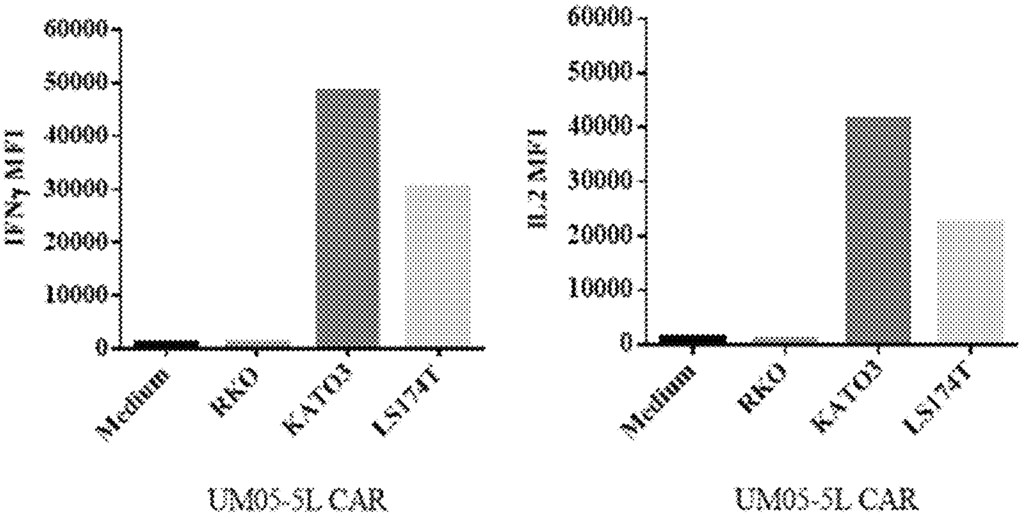
FIG. 6 showed the secretion of cytokines IFNγ (left) and IL-2 (right) after UM05-5L-CAR-T cells were mixed with tumor cells.

UM05-5L-CAR-T cells and CEACAM5-expressing tumor cells (for example, KATO3 and LS174T) were mixed, and a medium control (that was, only UM05-5L-CAR-T cells were used) and a CEACAM5 negative cell control (that was, UM05-5L-CAR-T cells and cells not expressing CEACAM5 such as RKO cells were used) were set; the two kinds of cells were mixed at a ratio of 1:1 and cultured for 16 hours, and the released IFNγ and IL2 in the supernatant were detected. The results were shown in FIG. 6, in which UM05-5L-CAR-T could recognize the cell line expressing CEACAM5 and induce the release of cytokines IFNγ and IL-2.

2. Detection of Killing Tumor Cells

Figure 7:
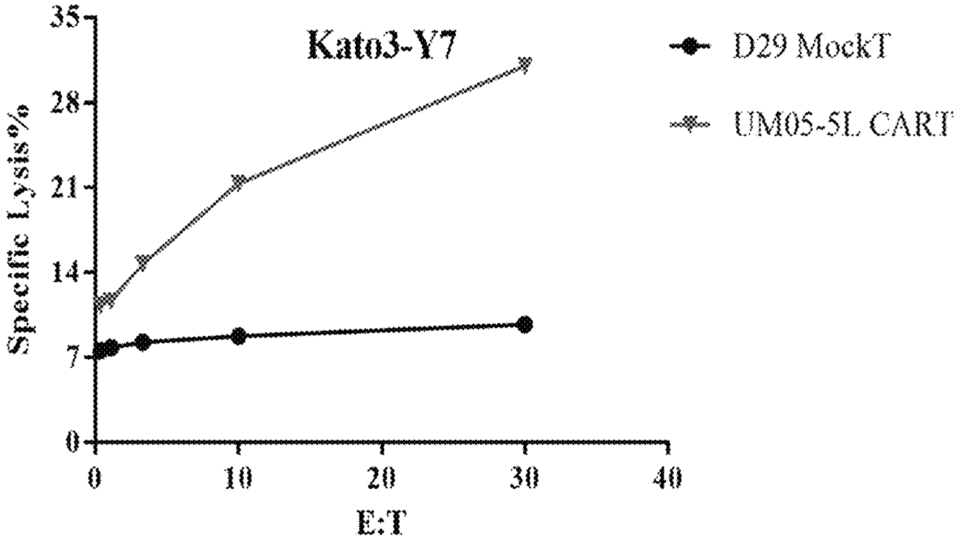
FIG. 7 showed the killing results of UM05-5L-CAR-T cells to tumor cell KATO3.

UM05-5L-CAR-T and CEACAM5-expressing tumor cells (for example, KATO3) were mixed and cultured in 96-well culture plate at a specified E:T ratio (30:1, 10:1, 3:1, 1:1, 0.3:1). Promega LDH detection kit was used to detect the release record data of lactate dehydrogenase (LDH) in the culture supernatant. The calculation results of killing tumor cells were shown in FIG. 7. It could be seen from the figure that UM05-5L-CAR-T killed tumor cells efficiently in a dose-dependent manner.

3. Proliferation Experiment Stimulated by Tumor Cells

Figure 8:
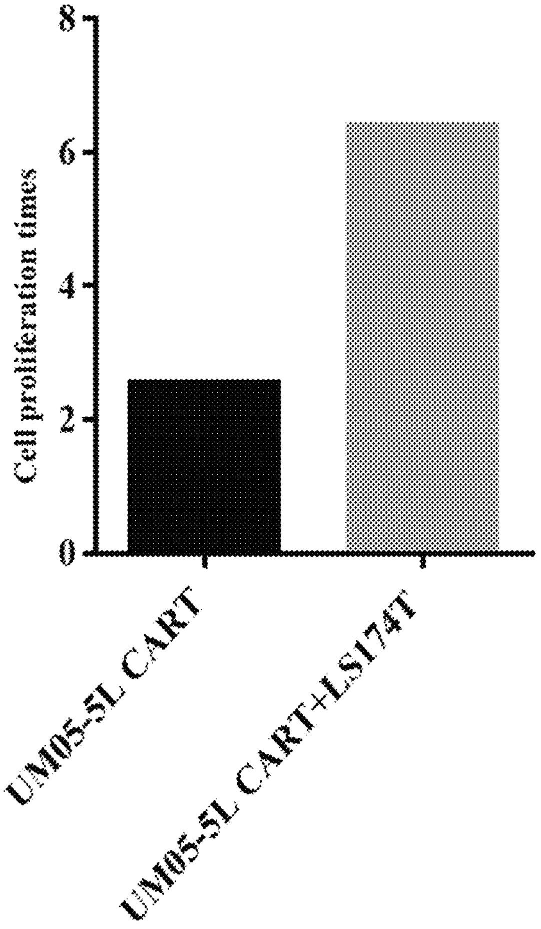
FIG. 8 showed the expansion of UM05-5L-CAR-T cells stimulated by tumor cell LS174T.

UM05-5L-CAR-T cells and CEACAM5-expressing tumor cells (for example, LS174T) were mixed and cultured for 72 hours (without IL2 supplement) according to E:T=1:1, and their proliferation was detected by cell counting. The results were shown in FIG. 8. UM05-5L-CAR-T could be efficiently proliferated when stimulated by the tumor cells expressing CEACAM5.

Example 8

In Vivo Pharmaceutical Efficacy Experiment of LS174T Tumor Model

Figure 9:
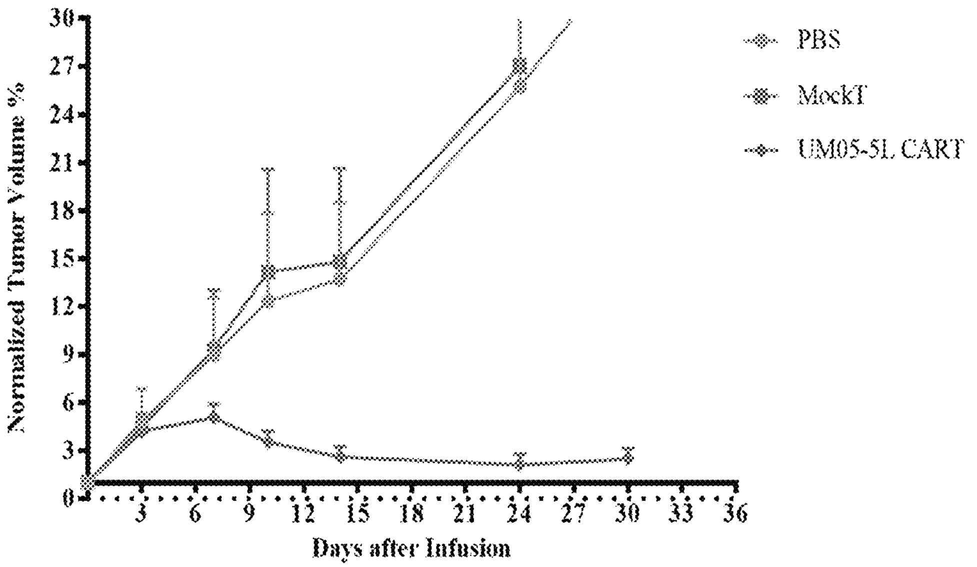
FIG. 9 showed the anti-tumor efficacy of UM05-5L-CAR-T cells in mice.
Figure 10:
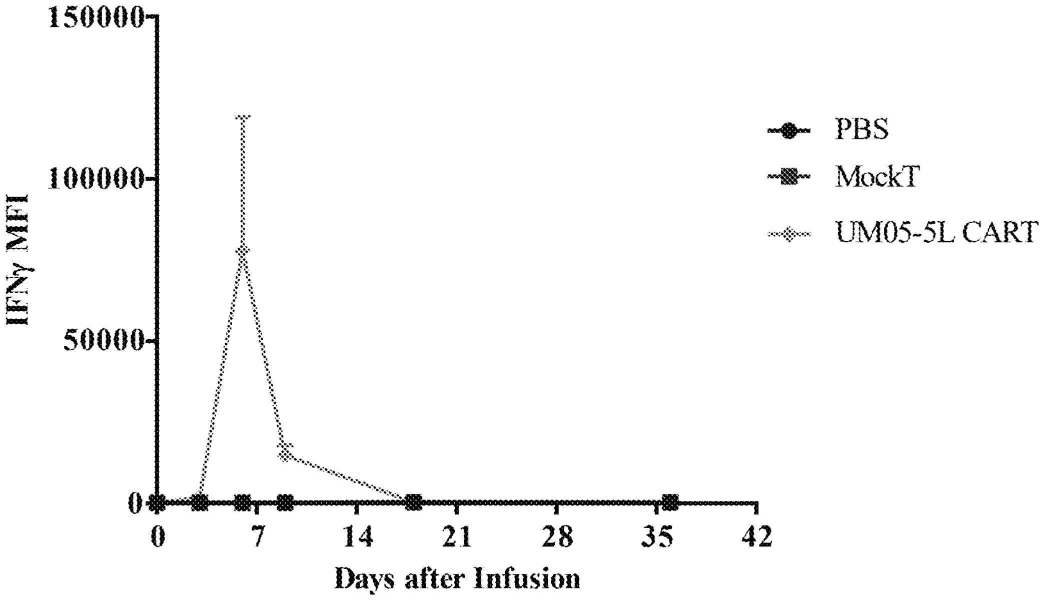
FIG. 10 showed the release of IFNγ in mice injected with UM05-5L-CAR-T cells.

LS174T cells (ATCC CL-187) were inoculated subcutaneously into NSG mice (Biocytometer) at $1\times10^7$/mouse. When the tumor volume reached 200 to 400 $mm^3$, PBS control, unmodified T cell control (Mock T) or UM05-5L CAR-T were administered via tail vein at doses of 100 μl, $1\times10^7$ cells, and $1\times10^7$ tEGFR+ cells, respectively. The tumor volume changes were recorded and the IFNγ release in peripheral blood was analyzed. The results were shown in FIG. 9 and FIG. 10. The UM05-5L recognized LS174T tumor cells in mice and released a large amount of IFNγ, resulting in strong tumor suppression effect.

Example 9

Preparation of Humanized Antibodies

The human antibody sequence in the IMGT database was used to humanize the UM05-5L antibody, and a humanized antibody was obtained, which was named hUM05-3. The specific sequence of hUM05-3 is shown in Table 6. The antibody preparation was carried out as described in Example 2. In short, the nucleotide sequences encoding SEQ ID NO: 16 and SEQ ID NO: 17 were synthesized, cloned into an expression vector, and transiently expressed in HEK293 cells, respectively. After culturing, the supernatant was collected and the antibody in the supernatant was purified by Protein A affinity chromatography. After the purification, the antibody was dialyzed with PBS solution, freeze-dried and concentrated, and stored at −20° C.

TABLE 6 hUM05-3 variable region sequences

| Monoclonal antibody | SEQ ID NO: VH | VL | HCDR1 | HCDR2 | HCDR3 | LCDR1 | LCDR2 | LCDR3 |
|---|---|---|---|---|---|---|---|---|
| hUM05-3 | 16 | 17 | 20 | 21 | 3 | 4 | 22 | 6 |

Example 10

Binding Ability of Humanized Antibody

LS174T cells (tumor cells with high expression of CEACAM5) were cultured in RPMI1640 medium containing 10% FBS. After digesting LS174T cells with TrypLE trypsin, the cells were centrifuged and resuspended in DPBS solution (FACS buffer, 4° C.) containing 2% BSA; then, the cells were added at $5\times10^5$/100 µL/well to the U-shaped bottom 96-well plate, and a series of dilution solutions of antibody were added to the U-shaped bottom 96-well plate, mixture was incubated at 4° C. for 1 hour. After incubation, the mixture was centrifuged and the resulted supernatant was discarded; 100 µl of secondary antibody (anti-human IgG Fc-APC) was added to each well, and incubated at 4° C. for 1 hour. After incubation, the cells were washed once with FACS buffer, resuspended in 200 µl FACS buffer, and the fluorescence signal value was read in BD C6 plus.

Figure 11:
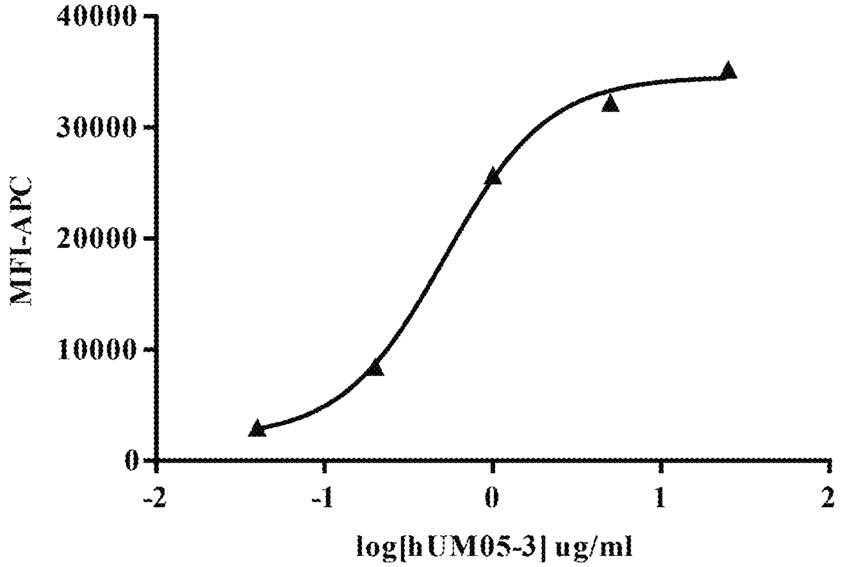
FIG. 11 showed the binding profile of the humanized antibody hUM05-3 to LS174T cells.

The experimental results are shown in FIG. 11. The results showed that the humanized antibody hUM05-3 could bind to LS174T cells in a dose-dependent manner.

Example 11

Mutations of Antibodies

Figure 12:
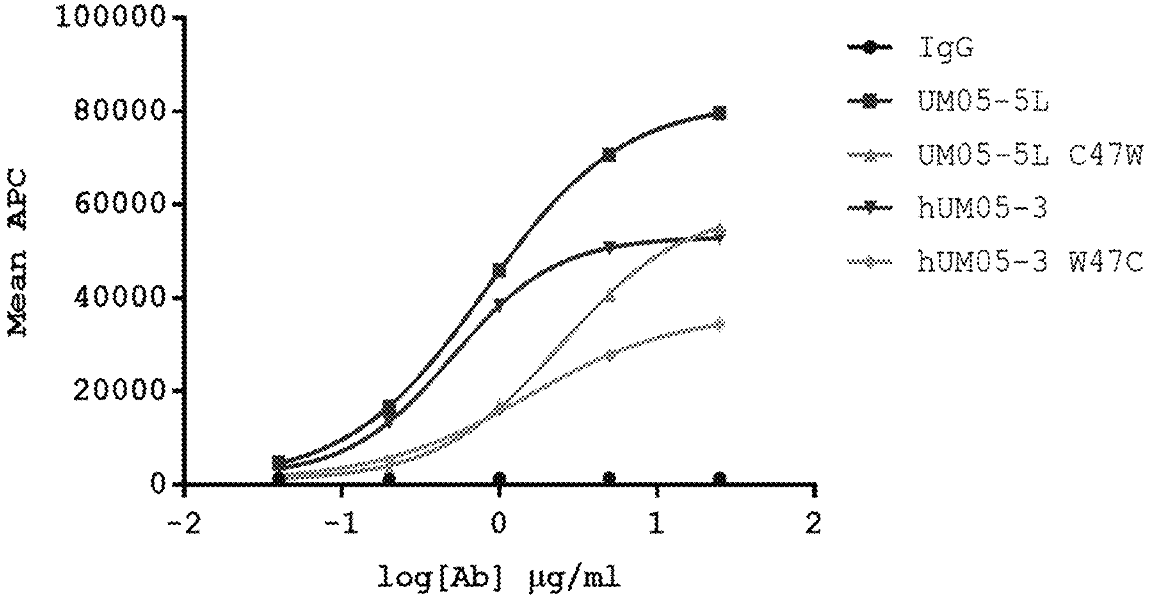
FIG. 12 showed the binding profile of the antibodies UM05-5L, UM05-5L C47W, hUM05-3 and hUM05-3 W47C to LS174T cells.

The 47th amino acid (Cys) of the human-mouse chimeric antibody UM05-5L VH was mutated to Trp, and the mutated antibody was named UM05-5L C47W; the 47th amino acid (Trp) of the humanized antibody hUM05-3 VH was mutated to Cys, and the mutated antibody was named hUM05-3 W47C. The variable region sequences of the mutated antibodies were shown in Table 7. As described in Example 10, the ability of the antibody binding to LS174T cells was tested. The experimental results were shown in FIG. 12 and Table 8. The results showed that the human-mouse chimeric antibody UM05-5L and the humanized antibody hUM05-3 could bind to cells expressing CEACAM5 before and after the mutation.

TABLE 7

| sequence of the mutated antibody | | |
|---|---|---|
| | VH | VL |
| UM05-5L C47W | SEQ ID NO: 18 | SEQ ID NO: 8 |
| hUM05-3 W47C | SEQ ID NO: 19 | SEQ ID NO: 17 |

TABLE 8

| Ability to bind to antigen | | |
|---|---|---|
| Monoclonal antibody | EC50 µg/ml | Emax MFI (Average fluorescence intensity) |
| UM05-5L | 0.81 | 79739 |
| UM05-5L C47W | 2.46 | 55153 |
| hUM05-3 | 0.53 | 52929 |
| hUM05-3 W47C | 1.47 | 34403 |

What is claimed is:

1. An antibody or antigen-binding fragment thereof that specifically binds to CEACAM5 protein, wherein the antibody or antigen-binding fragment thereof comprises:

(a) the following three heavy chain CDRs in a heavy chain variable region (VH): VH CDR1-consisting of the sequence of SEQ ID NO: 1, VH CDR2 consisting of the sequence of SEQ ID NO: 2, and VH CDR3 consisting of the sequence of SEQ ID NO: 3; and, the following three light chain CDRs in a light chain variable region (VL): VL CDR1 consisting of the sequence of SEQ ID NO: 4, VL CDR2 consisting of the sequence of SEQ ID NO: 5, and VL CDR3 consisting of the sequence of SEQ ID NO: 6; or (b) the following three heavy chain CDRs in a heavy chain variable region (VH): VH CDR1 consisting of the sequence of SEQ ID NO: 20, VH CDR2 consisting of the sequence of SEQ ID NO: 21, and VH CDR3 consisting of the sequence of SEQ ID NO: 3; and, the following three light chain CDRs in a light chain variable region (VL): VL CDR1 consisting of the sequence of SEQ ID NO: 4, VL CDR2 consisting of the sequence of SEQ ID NO: 22, and VL CDR3 consisting of the sequence of SEQ ID NO: 6.

2. The antibody or antigen-binding fragment thereof according to claim 1, wherein the antibody or antigen-binding fragment thereof comprises:

(a) VH consisting of the sequence of SEQ ID NO: 7 and VL consisting of the sequence of SEQ ID NO: 8;

(b) VH consisting of the sequence of SEQ ID NO: 18 and VL consisting of the sequence of SEQ ID NO: 8;

(c) VH consisting of the sequence of SEQ ID NO: 16 and VL consisting of the sequence of SEQ ID NO: 17; or (d) VH consisting of the sequence of SEQ ID NO: 19 and VL consisting of the sequence of SEQ ID NO: 17.

3. The antibody or antigen-binding fragment thereof according to claim 1, wherein the antibody or antigen-binding fragment thereof comprises a heavy chain constant region (CH) of a human immunoglobulin and a light chain constant region (CL) of a human immunoglobulin.

4. An isolated nucleic acid molecule, which encodes the antibody or antigen-binding fragment thereof according to claim 1.

5. A vector, which comprises the isolated nucleic acid molecule according to claim 4.

6. A host cell, which comprises the isolated nucleic acid molecule according to claim 4 or a vector comprising the isolated nucleic acid molecule.

7. A method for preparing the antibody or antigen-binding fragment thereof according to claim 1, which comprises: (i) culturing a host cell under a condition allowing expression of the antibody or antigen-binding fragment thereof, wherein the host cell comprises a nucleic acid molecule encoding the antibody or antigen-binding fragment thereof; and (ii) recovering the antibody or antigen-binding fragment thereof from a culture of the host cell.

8. A bispecific or multispecific molecule, which comprises the antibody or antigen-binding fragment thereof according to claim 1.

9. An immunoconjugate, which comprises the antibody or antigen-binding fragment thereof according to claim 1 and a therapeutic agent linked to the antibody or antigen-binding fragment thereof;

wherein, the immunoconjugate is characterized by one or more of the following:

(a) the therapeutic agent is a cytotoxic agent;

(b) the therapeutic agent is selected from the group consisting of alkylating agent, mitotic inhibitor, antitumor antibiotic, antimetabolite, topoisomerase inhibitor, tyrosine kinase inhibitor, radionuclide agent, and any combination thereof; and (c) the immunoconjugate is an antibody-drug conjugate (ADC).

10. A pharmaceutical composition, which comprises the antibody or antigen-binding fragment thereof according to claim 1, or a bispecific or multispecific molecule comprising the antibody or antigen-binding fragment thereof, or an immunoconjugate comprising the antibody or antigen-binding fragment thereof, with a pharmaceutically acceptable carrier and/or excipient.

11. A kit, which comprises the antibody or antigen-binding fragment thereof according to claim 1.

12. A chimeric antigen receptor, which comprises an antigen-binding domain of the antibody or antigen-binding fragment thereof according to claim 1;

wherein, the chimeric antigen receptor is characterized by one or more of the following:

(a) the antigen-binding domain comprises a heavy chain variable region and a light chain variable region of the antibody or antigen-binding fragment thereof according to claim 1; and (b) the antigen-binding domain is a scFv.

13. An isolated nucleic acid molecule, which encodes the chimeric antigen receptor according to claim 12.

14. A vector, which comprises the isolated nucleic acid molecule according to claim 13.

15. A host cell, which comprises the isolated nucleic acid molecule according to claim 13 or a vector comprising the isolated nucleic acid molecule;

wherein, the host cell is characterized by one or more of the following:

(a) the host cell is an immune effector cell;

(b) the host cell is T cell or NK cell; and (c) the host cell is a chimeric antigen receptor T cell (CAR-T).

16. A method for inhibiting growth of a tumor cell expressing CEACAM5 and/or killing the tumor cell, which comprises contacting the tumor cell with an effective amount of:

the antibody or antigen-binding fragment thereof according to claim 1.

17. A method for treating a tumor in a subject, the method comprising administering to a subject in need thereof an effective amount of:

the antibody or antigen-binding fragment thereof according to claim 1.

18. A method for detecting the presence or amount of CEACAM5 in a sample, which comprises the following steps:

(a) contacting the sample with the antibody or antigen-binding fragment thereof according to claim 1;

(b) detecting formation of a complex comprising the antibody or antigen-binding fragment thereof and CEACAM5, or detecting the amount of the complex;

wherein, the CEACAM5 is human CEACAM5.

19. A method for determining whether a tumor is capable of being treated by an anti-tumor therapy targeting CEACAM5, which comprises the following steps:

(a) contacting a sample containing a cell of the tumor with the antibody or antigen-binding fragment thereof according to claim 1;

(b) detecting formation of a complex comprising the antibody or antigen-binding fragment thereof and CEACAM5;

wherein, the method is characterized by one or more of the following:

(i) the CEACAM5 is human CEACAM5; and (ii) the tumor is selected from the group consisting of non-small cell lung cancer, small cell lung cancer, renal cell carcinoma, colorectal cancer, ovarian cancer, breast cancer, pancreatic cancer, gastric cancer, bladder cancer, esophageal cancer, mesothelioma, melanoma, head and neck cancer, thyroid cancer, sarcoma, prostate cancer, glioblastoma, cervical cancer, thymic cancer, leukemia, lymphoma, myeloma, mycosis fungoids, Merkel cell carcinoma hematological malignancies, primary mediastinal large B-cell lymphoma, T cell/histiocytic B-cell-rich lymphoma, EBV-positive and negative PTLD, EBV-related diffuse large B cell lymphoma (DLBCL), plasmablastic lymphoma, extranodal NK/T cell Lymphoma, nasopharyngeal carcinoma HHV8-related primary exudative lymphoma, Hodgkin's lymphoma, central nervous system (CNS) tumor, primary CNS lymphoma, spinal axis tumor, and brainstem glioma.

20. The antibody or antigen-binding fragment thereof according to claim 1, which is characterized by one or more of the following:

(a) the heavy chain constant region is an IgG heavy chain constant region;

(b) the heavy chain constant region has the sequence as shown in SEQ ID NO: 9;

(c) the light chain constant region is a k light chain constant region;

(d) the light chain constant region has the sequence as shown in SEQ ID NO: 11;

(e) the antigen-binding fragment is selected from the group consisting of Fab, Fab', (Fab')2, Fv, disulfide-linked Fv, BsFv, DsFv, (dsFv)2, dsFv-dsFv', scFv, scFv dimer, camelized single chain domain antibody, diabody, ds diabody, nanobody, single domain antibody (sdAb), bivalent domain antibody; and/or, the antibody is a murine antibody, chimeric antibody, humanized antibody, bispecific antibody or multispecific antibody; and (f) the antibody or antigen-binding fragment thereof comprises a label.

21. The bispecific or multispecific molecule according to claim 8, which is characterized by one or more of the following:

(a) the bispecific or multispecific molecule specifically binds to CEACAM5, and additionally specifically binds to one or several other targets;

(b) the bispecific or multispecific molecule further comprises at least one molecule having a second binding specificity for a second target; and (c) the bispecific or multispecific molecule further comprises a second antibody.

22. The pharmaceutical composition according to claim 10, the pharmaceutical composition comprises an additional pharmaceutically active agent;

wherein, the pharmaceutical composition is characterized by one of the following:

(a) the additional pharmaceutically active agent is a drug with an anti-tumor activity;

(b) the additional pharmaceutically active agent is an alkylating agent, mitotic inhibitor, anti-tumor antibiotic, antimetabolite, topoisomerase inhibitor, tyrosine kinase inhibitor, radionuclide, radiosensitizer, anti-angiogenesis agent, cytokine, molecular targeted drug, immune checkpoint inhibitor or oncolytic virus; or (c) the antibody or antigen-binding fragment thereof, bispecific or multispecific molecule or immunoconjugate and the additional pharmaceutically active agent are provided as separate components or as components of the same composition.

23. The kit according to claim 11, wherein the antibody or antigen-binding fragment thereof and/or the second antibody comprises a detectable label.

24. A method for inhibiting growth of a tumor cell expressing CEACAM5 and/or killing the tumor cell, which comprises contacting the tumor cell with an effective amount of a bispecific or multispecific molecule comprising the antibody or antigen-binding fragment according to claim 1.

25. A method for inhibiting growth of a tumor cell expressing CEACAM5 and/or killing the tumor cell, which comprises contacting the tumor cell with an effective amount of an immunoconjugate comprising the antibody or antigen-binding fragment according to claim 1.

26. A method for inhibiting growth of a tumor cell expressing CEACAM5 and/or killing the tumor cell, which comprises contacting the tumor cell with an effective amount of a pharmaceutical composition comprising the antibody or antigen-binding fragment according to claim 1.

27. A method for inhibiting growth of a tumor cell expressing CEACAM5 and/or killing the tumor cell, which comprises contacting the tumor cell with an effective amount of a chimeric antigen receptor comprising the antibody or antigen-binding fragment according to claim 1.

28. A method for inhibiting growth of a tumor cell expressing CEACAM5 and/or killing the tumor cell, which comprises contacting the tumor cell with an effective amount of the host cell according to claim 15.

29. A method for treating a tumor in a subject, the method comprising administering to a subject in need thereof an effective amount of a bispecific or multispecific molecule comprising the antibody or antigen-binding fragment according to claim 1.

30. A method for treating a tumor in a subject, the method comprising administering to a subject in need thereof an effective amount of an immunoconjugate comprising the antibody or antigen-binding fragment according to claim 1.

31. A method for treating a tumor in a subject, the method comprising administering to a subject in need thereof an effective amount of a pharmaceutical composition comprising the antibody or antigen-binding fragment according to claim 1.

32. A method for treating a tumor in a subject, the method comprising administering to a subject in need thereof an effective amount of a chimeric antigen receptor comprising the antibody or antigen-binding fragment according to claim 1.

33. A method for treating a tumor in a subject, the method comprising administering to a subject in need thereof an effective amount of the host cell according to claim 15.

* * * * *

SEQUENCE LISTING

```
<160> NUMBER OF SEQ ID NOS: 22

<210> SEQ ID NO 1
<211> LENGTH: 5
<212> TYPE: PRT
<213> ORGANISM: artificial
<220> FEATURE:
<223> OTHER INFORMATION: UM05-5L VH CDR1

<400> SEQUENCE: 1

Asp His Thr Ile His
1               5


<210> SEQ ID NO 2
<211> LENGTH: 17
<212> TYPE: PRT
<213> ORGANISM: artificial
<220> FEATURE:
<223> OTHER INFORMATION: UM05-5L VH CDR2

<400> SEQUENCE: 2

Tyr Ile Tyr Pro Arg Asp Gly Asn Thr Lys Tyr Asn Glu Lys Phe Lys
1               5                   10                  15

Gly


<210> SEQ ID NO 3
<211> LENGTH: 10
<212> TYPE: PRT
<213> ORGANISM: artificial
<220> FEATURE:
<223> OTHER INFORMATION: UM05-5L VH CDR3

<400> SEQUENCE: 3

Pro Ile Tyr Asp Gly Tyr Ser Phe Asp Tyr
1               5                   10
```

<210> SEQ ID NO 4
<211> LENGTH: 10
<212> TYPE: PRT
<213> ORGANISM: artificial
<220> FEATURE:
<223> OTHER INFORMATION: UM05-5L VL CDR1

<400> SEQUENCE: 4

```
Arg Ala Ser Ser Ser Val Ser Tyr Met His
1               5                   10
```

<210> SEQ ID NO 5
<211> LENGTH: 7
<212> TYPE: PRT
<213> ORGANISM: artificial
<220> FEATURE:
<223> OTHER INFORMATION: UM05-5L VL CDR2

<400> SEQUENCE: 5

```
Asp Thr Ser Lys Leu Ala Ser
1               5
```

<210> SEQ ID NO 6
<211> LENGTH: 9
<212> TYPE: PRT
<213> ORGANISM: artificial
<220> FEATURE:
<223> OTHER INFORMATION: UM05-5L VL CDR3

<400> SEQUENCE: 6

```
Gln Gln Trp Thr Arg Asn Pro Pro Thr
1               5
```

<210> SEQ ID NO 7
<211> LENGTH: 119
<212> TYPE: PRT
<213> ORGANISM: artificial
<220> FEATURE:
<223> OTHER INFORMATION: UM05-5L VH

<400> SEQUENCE: 7

```
Gln Val Gln Leu Gln Gln Ser Asp Ala Asp Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Cys Ile
        35                  40                  45

Gly Tyr Ile Tyr Pro Arg Asp Gly Asn Thr Lys Tyr Asn Glu Lys Phe
    50                  55                  60

Lys Gly Lys Ala Thr Leu Thr Ala Asp Arg Ser Ser Ile Thr Ala Tyr
65                  70                  75                  80

Met Gln Leu Asn Ser Leu Thr Ser Glu Asp Ser Ala Val Tyr Phe Cys
                85                  90                  95

Ala Arg Pro Ile Tyr Asp Gly Tyr Ser Phe Asp Tyr Trp Gly Gln Gly
            100                 105                 110

Thr Thr Leu Thr Val Ser Ser
        115
```

<210> SEQ ID NO 8
<211> LENGTH: 106
<212> TYPE: PRT
<213> ORGANISM: artificial
<220> FEATURE:
<223> OTHER INFORMATION: UM05-5L VL

<400> SEQUENCE: 8

Gln Ile Val Leu Thr Gln Ser Pro Ala Ile Met Ser Ala Ser Pro Gly
1 5 10 15

Glu Lys Val Thr Met Thr Cys Arg Ala Ser Ser Ser Val Ser Tyr Met
20 25 30

His Trp Tyr Gln Gln Lys Ser Gly Thr Ser Pro Lys Arg Trp Ile Tyr
35 40 45

Asp Thr Ser Lys Leu Ala Ser Gly Val Pro Ala Arg Phe Ser Gly Ser
50 55 60

Gly Ser Gly Thr Ser Tyr Ser Leu Thr Ile Ser Ser Met Ala Ala Glu
65 70 75 80

Asp Ala Ala Thr Tyr Tyr Cys Gln Gln Trp Thr Arg Asn Pro Pro Thr
85 90 95

Phe Gly Ala Gly Thr Lys Leu Glu Leu Lys
100 105

<210> SEQ ID NO 9
<211> LENGTH: 330
<212> TYPE: PRT
<213> ORGANISM: artificial
<220> FEATURE:
<223> OTHER INFORMATION: IgG1 heavy chain constant region

<400> SEQUENCE: 9

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 10
<211> LENGTH: 993
<212> TYPE: DNA
<213> ORGANISM: artificial
<220> FEATURE:
<223> OTHER INFORMATION: Nucleotide sequence encoding IgG1 heavy chain constant region

<400> SEQUENCE: 10

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggaccccc    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa tga                                 993
```

<210> SEQ ID NO 11
<211> LENGTH: 107
<212> TYPE: PRT
<213> ORGANISM: artificial
<220> FEATURE:
<223> OTHER INFORMATION: kappa chain constant region

<400> SEQUENCE: 11

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 12
<211> LENGTH: 324
<212> TYPE: DNA
<213> ORGANISM: artificial
<220> FEATURE:
<223> OTHER INFORMATION: Nucleotide sequence encoding kappa chain
      constant region

<400> SEQUENCE: 12

cgtacggtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagttcgcc cgtcacaaag     300

agcttcaaca ggggagagtg ttga                                            324


<210> SEQ ID NO 13
<211> LENGTH: 240
<212> TYPE: PRT
<213> ORGANISM: artificial
<220> FEATURE:
<223> OTHER INFORMATION: VH-G4S3-VL

<400> SEQUENCE: 13

Gln Val Gln Leu Gln Gln Ser Asp Ala Asp Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Cys Ile
        35                  40                  45

Gly Tyr Ile Tyr Pro Arg Asp Gly Asn Thr Lys Tyr Asn Glu Lys Phe
    50                  55                  60

Lys Gly Lys Ala Thr Leu Thr Ala Asp Arg Ser Ser Ile Thr Ala Tyr
65                  70                  75                  80

Met Gln Leu Asn Ser Leu Thr Ser Glu Asp Ser Ala Val Tyr Phe Cys
                85                  90                  95

Ala Arg Pro Ile Tyr Asp Gly Tyr Ser Phe Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met His Trp Tyr Gln Gln Lys Ser Gly Thr Ser
```

```
                165                 170                 175

Pro Lys Arg Trp Ile Tyr Asp Thr Ser Lys Leu Ala Ser Gly Val Pro
            180                 185                 190

Ala Arg Phe Ser Gly Ser Gly Ser Gly Thr Ser Tyr Ser Leu Thr Ile
        195                 200                 205

Ser Ser Met Ala Ala Glu Asp Ala Ala Thr Tyr Tyr Cys Gln Gln Trp
    210                 215                 220

Thr Arg Asn Pro Pro Thr Phe Gly Ala Gly Thr Lys Leu Glu Leu Lys
225                 230                 235                 240


<210> SEQ ID NO 14
<211> LENGTH: 357
<212> TYPE: DNA
<213> ORGANISM: artificial
<220> FEATURE:
<223> OTHER INFORMATION: UM05-5L VH gene

<400> SEQUENCE: 14

caggttcagc tgcaacagtc tgacgctgac ttggtgaaac ctggagcttc agtgaagata      60

tcctgcaagg tctctggcta caccttcact gaccatacta ttcactggat gaagcagagg     120

cctgaacagg gcctggaatg cattggatat atttatccta gagatggtaa tactaagtac     180

aatgagaagt tcaagggcaa ggccacattg actgcagaca gatcctccat cacagcctac     240

atgcagctca acagcctgac atctgaggac tctgcagtct atttctgtgc aagacccatc     300

tatgatggtt actcctttga ctactggggc caaggcacca ctctcacagt ctcctca        357


<210> SEQ ID NO 15
<211> LENGTH: 318
<212> TYPE: DNA
<213> ORGANISM: artificial
<220> FEATURE:
<223> OTHER INFORMATION: UM05-5L VL gene

<400> SEQUENCE: 15

caaattgttc tcacccagtc tccagcaatc atgtctgcat ctccagggga gaaggtcacc      60

atgacctgcc gtgccagctc aagtgttagt tacatgcact ggtaccagca gaagtcaggc     120

acctccccca aaagatggat ttatgacaca tccaaactgg cttctggagt ccctgctcgc     180

ttcagtggca gtgggtctgg gacctcttac tctctcacaa tcagcagcat ggcggctgaa     240

gatgctgcca cttattactg ccagcagtgg actcgtaacc cacctacctt cggtgctggg     300

accaagctgg agctgaaa                                                   318


<210> SEQ ID NO 16
<211> LENGTH: 119
<212> TYPE: PRT
<213> ORGANISM: artificial
<220> FEATURE:
<223> OTHER INFORMATION: hUM05-3 VH

<400> SEQUENCE: 16

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Met His Trp Met Gln Gln Ala Pro Gly Gln Gly Leu Glu Trp Ile
        35                  40                  45

Gly Leu Ile Tyr Pro Arg Asp Gly Ser Thr Ile Tyr Asn Glu Lys Phe
    50                  55                  60
```

```
Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Arg Pro Ile Tyr Asp Gly Tyr Ser Phe Asp Tyr Trp Gly Gln Gly
            100                 105                 110

Thr Leu Val Thr Val Ser Ser
        115


<210> SEQ ID NO 17
<211> LENGTH: 106
<212> TYPE: PRT
<213> ORGANISM: artificial
<220> FEATURE:
<223> OTHER INFORMATION: hUM05-3 VL

<400> SEQUENCE: 17

Gln Ile Val Leu Thr Gln Ser Pro Ala Thr Leu Ser Ala Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Lys Arg Trp Ile Tyr
        35                  40                  45

Asp Thr Ser Asn Arg Ala Thr Gly Val Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Ala Ala Val Tyr Tyr Cys Gln Gln Trp Thr Arg Asn Pro Pro Thr
                85                  90                  95

Phe Gly Gln Gly Thr Lys Leu Glu Leu Lys
            100                 105


<210> SEQ ID NO 18
<211> LENGTH: 119
<212> TYPE: PRT
<213> ORGANISM: artificial
<220> FEATURE:
<223> OTHER INFORMATION: UM05-5L C47W VH

<400> SEQUENCE: 18

Gln Val Gln Leu Gln Gln Ser Asp Ala Asp Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Asn Thr Lys Tyr Asn Glu Lys Phe
    50                  55                  60

Lys Gly Lys Ala Thr Leu Thr Ala Asp Arg Ser Ser Ile Thr Ala Tyr
65                  70                  75                  80

Met Gln Leu Asn Ser Leu Thr Ser Glu Asp Ser Ala Val Tyr Phe Cys
                85                  90                  95

Ala Arg Pro Ile Tyr Asp Gly Tyr Ser Phe Asp Tyr Trp Gly Gln Gly
            100                 105                 110

Thr Thr Leu Thr Val Ser Ser
        115
```

<210> SEQ ID NO 19
<211> LENGTH: 119
<212> TYPE: PRT
<213> ORGANISM: artificial
<220> FEATURE:
<223> OTHER INFORMATION: hUM05-3 W47C VH

<400> SEQUENCE: 19

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Met His Trp Met Gln Gln Ala Pro Gly Gln Gly Leu Glu Cys Ile
        35                  40                  45

Gly Leu Ile Tyr Pro Arg Asp Gly Ser Thr Ile Tyr Asn Glu Lys Phe
    50                  55                  60

Gln Gly Arg Ala Thr Leu Thr Ala Asp Arg Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Arg Pro Ile Tyr Asp Gly Tyr Ser Phe Asp Tyr Trp Gly Gln Gly
            100                 105                 110

Thr Leu Val Thr Val Ser Ser
        115
```

<210> SEQ ID NO 20
<211> LENGTH: 5
<212> TYPE: PRT
<213> ORGANISM: artificial
<220> FEATURE:
<223> OTHER INFORMATION: hUM05-3 VH CDR1

<400> SEQUENCE: 20

```
Asp His Thr Met His
1               5
```

<210> SEQ ID NO 21
<211> LENGTH: 17
<212> TYPE: PRT
<213> ORGANISM: artificial
<220> FEATURE:
<223> OTHER INFORMATION: hUM05-3 VH CDR2

<400> SEQUENCE: 21

```
Leu Ile Tyr Pro Arg Asp Gly Ser Thr Ile Tyr Asn Glu Lys Phe Gln
1               5                   10                  15

Gly
```

<210> SEQ ID NO 22
<211> LENGTH: 7
<212> TYPE: PRT
<213> ORGANISM: artificial
<220> FEATURE:
<223> OTHER INFORMATION: hUM05-3 VL CDR2

<400> SEQUENCE: 22

```
Asp Thr Ser Asn Arg Ala Thr
1               5
```